United States Patent [19]

Carney

[11] Patent Number: 5,443,956
[45] Date of Patent: Aug. 22, 1995

[54] DETECTION, QUANTITATION AND CLASSIFICATION OF RAS PROTEINS IN BODY FLUIDS AND TISSUES

[75] Inventor: Walter P. Carney, Brighton, Mass.

[73] Assignee: Oncogene Science, Inc., Uniondale, N.Y.

[21] Appl. No.: 78,485

[22] Filed: Jun. 17, 1993

Related U.S. Application Data

[63] Continuation of Ser. No. 815,577, Dec. 27, 1991, abandoned, which is a continuation of Ser. No. 334,823, Apr. 11, 1989, abandoned, which is a continuation-in-part of Ser. No. 185,582, Apr. 22, 1988, abandoned, and a continuation-in-part of Ser. No. 185,194, Apr. 22, 1988, abandoned, and a continuation-in-part of Ser. No. 71,175, Jul. 8, 1987, Pat. No. 5,081,230, and a continuation-in-part of Ser. No. 158,730, Feb. 22, 1988, Pat. No. 5,028,527, and a continuation-in-part of Ser. No. 111,315, Oct. 22, 1987, Pat. No. 4,898,932, which is a continuation-in-part of Ser. No. 913,905, Oct. 1, 1986, abandoned, and a continuation-in-part of Ser. No. 696,197, Jan. 29, 1985, abandoned.

[51] Int. Cl.[6] .............. G01N 33/573; G01N 33/574; G01N 33/577
[52] U.S. Cl. .................... 435/7.23; 435/7.4; 435/7.94; 436/578; 436/548; 436/813
[58] Field of Search ............ 435/7.23, 7.94, 7.4; 436/578, 548, 813

[56] References Cited

U.S. PATENT DOCUMENTS

| | | | |
|---|---|---|---|
| 4,228,237 | 10/1980 | Hevey et al. | 435/7 |
| 4,504,585 | 3/1985 | Reynolds | 436/518 |
| 4,535,058 | 8/1985 | Weinberg et al. | 435/6 |
| 4,568,640 | 2/1986 | Rubin | 435/70 |
| 4,690,890 | 9/1987 | Loor et al. | 436/531 |
| 4,699,877 | 10/1987 | Cline et al. | 435/6 |
| 4,725,550 | 2/1988 | Perucho et al. | 435/320 |
| 4,762,706 | 8/1988 | McCormick et al. | 424/85 |
| 4,786,718 | 1/1988 | Weinberg et al. | 530/387 |
| 4,798,787 | 1/1989 | McCormick et al. | 435/7 |
| 4,820,631 | 4/1989 | Lacal et al. | 435/6 |

(List continued on next page.)

FOREIGN PATENT DOCUMENTS

| | | |
|---|---|---|
| 0108564 | 5/1984 | European Pat. Off. . |
| 0190033 | 8/1986 | European Pat. Off. . |
| 0310132 | 4/1989 | European Pat. Off. . |
| 259197 | 12/1985 | Japan . |

(List continued on next page.)

OTHER PUBLICATIONS

Caruso et al., Int. J. Cancer, pp. 587–595, vol. 38 (1986).
Hand et al., Biochem. Biophys. Acta. 908(2):131–142 (1987).
Haand et al. JNCI 79(1):59–66 (1987).
Niman et al., Clin. Lab. Med. (US), 6(1):181–196 (Mar. 1986).
Niman et al., Proc. Natl. Acad. Sci. USA, pp. 7924–7928, vol. 82 (Dec. 1985).
Ohuchi et al., Can. Res. 47(5):1413–1420 (1987).
Ohuchi et al., Can. Res., pp. 2511–2519, vol. 46 (May 1986).
CA 106:174296y, pp. 550, vol. 106 (1987).
Andreff et al., Blood, pp. 676–681, vol. 87, No.3 (Mar. 1986).
Bizub et al., Oncogene, pp. 131–142, vol. 1 (1987).
Bos et al., Nature, pp. 726–730, vol. 315, (Jun. 27, 1985).
Carney et al., 78th Ann. Mtg. at Amer. Assn. for Can. Res., May 20–23, 1987.
Carney et al., UCLA Symposia, Jan. 20–Feb. 15, 1986, (List continued on next page.)

Primary Examiner—David Saunders
Attorney, Agent, or Firm—John P. White

[57] ABSTRACT

Detection, quantitation and classification of ras p21 proteins in body fluids, tissues, or cells is described. Specifically, this disclosure concerns detecting and quantitating normal and mutated ras p21s from normal subjects, subjects suspected of having preneoplastic disease or subjects known or suspected of having neoplastic (cancer) disease. This invention also concerns the detection and quantitation of the ras p21 proteins into the three families of ras proteins designated Ha, Ki and N in body fluids and tissues.

6 Claims, 14 Drawing Sheets

U.S. PATENT DOCUMENTS

| | | | |
|---|---|---|---|
| 4,871,838 | 10/1989 | Bos et al. | 536/27 |
| 4,898,932 | 2/1990 | Carney | 530/387 |
| 4,957,859 | 9/1990 | Bizub et al. | 435/7 |
| 5,015,571 | 5/1991 | Niman et al. | 435/7.92 |

(List continued on next page.)

FOREIGN PATENT DOCUMENTS

| | | |
|---|---|---|
| WO82/00204 | 1/1982 | WIPO . |
| WO84/03087 | 8/1984 | WIPO . |
| WO85/00807 | 2/1985 | WIPO . |

OTHER PUBLICATIONS

Steamboat Springs, Colorado; Alan N. Liss, Inc., NY Jour. Cell. Bio., Suppl. 10A (1986).
Carney et al., Fifth Ann. Congress for Hybridoma Res., Jan. 26–29, 1986, Balti., MD; Hybridoma 5(1).
Carney et al., Lab. Invest. 54:10A, Jan. 1986.
Carney et al., Lab. Invest. 58 (1988).
Carney et al., J. Cell. Bio., pp. 207–214, vol. 32 (1986).
Carney et al., Intl. Acad. Pathol., Mar. 1987; Lab Invest. 56(1)11A. abstract No. 59.
Carney et al., Intl. Acad. Path., Mar. 1987; Lab invest. 569(1)11A. abstract No. 60.
Carney et al., Third Ann. Mtg. on Oncogenes, Frederick, MD (1987).
Carney et al., Monoclonal Antibodies & Cancer Therapy, pp. 565–572. (1985).
Carney et al., 69th Ann. Mtg. FASEB (Apr. 1985).
Carney et al., Apr. 1986 Mtg. FASEB.
Carney et al., PNAS (USA), pp. 7485–7489, vol. 83 (Oct. 1986).
Carney et al., UCLA Symp. Mol. Cell. Biol. New. Ser., pp. 565–572, vol. 27 (1985); CA vol. 104(1986), No. 166570B.
Carney et al., 20th Ann. Oak Ridge Conf. on Advanced Analytical Concepts for Clin. Labs (Apr. 1988).
Carney et al., Dupont Biotechnology Update , p. 16 (Apr. 1988).
Chang et al., Nature, pp. 479–483, vol. 297 (Jun. 10, 1982).
Clanton et al., Mol. Cell. Biol., pp. 3092–3097, vol. 7, No. 9 (1987).
Clark et al., Biochemica et Biophysica Acta, pp. 9–20, vol. 738 (1984).
Clark et al., PNAS (USA), pp. 5280–5284, vol. 82, No. 16 (Aug. 1985).
Cooper et al., Biochimica et Biophysica Acta, pp. 9–20, vol. 738 (1984).
Der et al., Cell, pp. 167–176, vol. 44 (Jan. 17, 1986).
Faramo et al., J. Mol. Appl. Genet, 2(2):173–180 (1983).
Feramisco et al., Nature (England), 314 (6012): 639–642 (Apr. 18–24, 1985).
Finkel et al., Cell. pp. 151–158, vol. 37 (May 1984).
Freedman et al., In Vitro Cellular Developmental Biology, pp. 621–624, vol. 22, No. 10 (Oct. 1986).
Furth et al., J. of Virology, pp. 294–304, vol. 43 No. 1 (Jul. 1982).
Gallick et al., PNAS, pp. 1795–1799, vol. 82, Mar. 1985.
Gambke et al., Nature, pp. 476–478, vol. 307, (Feb. 2, 1984).
Ghosh et al., J. Clin. Pathol. (England), pp. 428–434, vol. 39, No. 4 (Apr. 1986).
Gibbs et al., PNAS (USA), pp. 5704–5708, vol. 81 (Sep. 1984).
Hamer et al., 72nd Ann, Mtg. FASEB, May 1–5, 1988, Las Vegas, Nev.
Hamer et al., Amer. Commer. & Indus. Conf. & Expo in Biotechnology, Apr, 27–May 1, 1986, Boston, MA.
Hand et al., PNAS pp. 5227–5231, vol. 81 (Aug. 1984).
Herlyn et al., J. Clin. Immun., pp. 135–140, vol. 2, No. 2. (1982).
Hirai et al., nature, pp. 430–432, vol. 327 (Jun. 4, 1987).
Ho et al., FASEB, vol. 46(3) (1987).
Kurzrock et al., Can. Res., pp. 1530–1534, vol. 46 (Mar. 1986).
Lacal et al., Mol. & Cell. Biol., pp. 1002–1009, vol. 6 No,4 (Apr. 1986).
Lee et al., Lab Invest. 56:42A (Mar. 1987).
Lefbvre et al., Lab. invest. 54:35a (Jan. 1986).
Liu et al., Nature, pp. 186–188, vol. 330 (Nov. 12, 1987).
Manne et al., PNAS (USA), pp. 376–380, vol. 82 (Jan. 1985).
McGrath et al., Nature, pp. 644–649, vol. 310, No. 23 (Aug. 1984).
Metzgar et al., Can. Res., pp. 601–608, vol. 42 (Feb. 1982).
Moore et al., Nature, pp. 733–734, vol. 327 (Jun 25, 1987).
Nishida et al., Biochem. Biophys. Res. Common. 146(1):247–252.

(List continued on next page.)

U.S. PATENT DOCUMENTS

| | | | |
|---|---|---|---|
| 5,028,527 | 7/1991 | Carney | 435/7.92 |
| 5,081,230 | 1/1992 | Carney | 530/387 |
| 5,084,380 | 1/1992 | Carney | 435/7.23 |
| 5,112,737 | 5/1992 | Carney | 435/7.92 |

OTHER PUBLICATIONS

Nitta et al., Jpn. J. Res. (Gann). pp. 21–26, vol. 78 (Jan. 1987).

Papageorge et al., J. of Virol., pp. 509–519, vol. 519, vol. 44, No. 2 (Nov. 1982).

Parada et al., Nature, pp. 474–476, vol. 297 (Jun. 10, 1982).

Poe et al., J. Biol. Chem., pp. 3906–3909, vol. 260, No. 7 (Apr. 10, 1985).

Radosevich et al., Amer. Fed. Clin. Res., Sep. 1987, Chicago, Il.

Reddy et al., Nature, pp. 149–152, vol. 300 (Nov. 11, 1982).

Robinson et al., Br, J. Cancer, pp. 877–883, vol. 54 (1986).

Santos et al., Science, pp. 661–664, vol. 223 (Feb. 17, 1984).

Santos et al., Nature, pp. 343–344, vol. 298, (Jul. 22, 1982).

Schlom, Fifth Ann. Congress for Hybridoma Res., pp. 165–166, Jan. 26–29, 1986, Baltimore, Md.

Scolnick et al., PNAS (USA), pp. 5355–5359, vol. 76 (Oct. 1979).

Sevier et al., Clin. Chem., pp. 1797–1806, vol. 27, No. 11 (1981).

Shilo et al., Nature, pp. 607–609, vol. 289 (Feb. 12, 1981).

Shimizu et al., Nature, 304(5926), pp. 497–500 (1983).

Srivastava et al., Mol. & Cell. Biol., pp. 3316–3319, vol. 5, No. 22, (Nov. 1985).

Tabin et al., Nature, pp. 143–149, vol. 300 (Nov. 11, 1982).

Tahara et al., Jpn. J. Can. Res. (Gann). pp. 517–522 (1986).

Tanaka et al., Can. Res., pp. 1465–1470, vol. 46 (Mar. 1986).

Tanaka et al., PNAS (USA), pp. 3400–3404, vol. 82 (May 1985).

Taparowsky et al., Banbury Report, 14:123–133 (1983); Chem. Abs, CA 100(1):1425n.

Taparowsky et al., Cell, pp. 581–586, vol. 34 (1983).

Thor et al., Nature, pp. 562–565, vol. 311 (Oct. 11, 1984).

Trimpe et al., Third Ann. Mtg on Oncogenes (1987).

Trimpe et al., Intl. Acad. Pathol., US & Can. Div., Feb. 29–Mar. 3, 1988, Wash. D.C.; Lab Invest. 58.

Wodnar-Filpowicz et al., Oncogene, pp. 457–461, vol. 1, No. 4 (1987).

Wolfe et al., Lab. Invest. 52:77a (1985).

Wong et al., Can. Res, pp. 6029–6033, vol. 46 (Dec. 1986).

Yuasa et al., Nature, pp. 775–779, vol. 303 (Jun. 30, 1983).

Zarbl et al., Nature, pp. 382–385, vol. 315 (May 30, 1985).

Bizub et al., Cancer Research 49:6425–6431 (Nov. 15, 1989).

Hamer et al., Hybridoma 9:573–587 (1990).

LaVecchio et al., Oncogene 5:1173–1178 (1990).

Kennel, J. Immunological Methods 55:172 (1982).

Dierks et al., Molec. Immunol. 23(4):403–411 (1986).

Jansson et al., Cancer, pp. 1329–1337, vol. 65 (Mar. 15, 1990).

Ng et al. "Plasma Detection of Activated Ras p21 Expression in MMTV/V-HA RAS Transgenic Mice" Abstract, Sixth Annual Meeting on Ocogenes, 1990.

Hamer et al., "Quantitation of HER-2/Neu Proteins in Breast and Ovarian Carcinomas" Abstract, Sixth Annual Meeting on Oncogenes, 1990.

Brandt-Rauf et al., Br. J. Industrial Medicine, 45:689–693 (1988).

Wolfman et al., J. Biol. Chem., pp. 10820–10827, vol. 224, No. 18 (1989).

Carney et al., Analysis of Ras Oncogene Proteins (p21) in Tumor Cells Using Flow Cytometry and Immunohistochemistry, 8th International Congress of Histochemistry and Cytochemistry, Aug. 1988.

Carney et al., Detection of Activated Ras Proteins in Human and Animal Cancers Using Monoclonal Antibodies, American Association for Clinical Chemistry, New Orleans, Louisiana, Jul. 24–28, 1988.

Carney et al., Human Tumor Antigens and Specific Tumor Therapy, pp. 53–62 (1989).

Carney et al., Monoclonal Antibodies for the Detection of Activated and Norman Ras p21s in Neoplastic and Preneoplastic Cells, Human Tumor Antigens and Specific Tumor Therapy, UCLA Symposium Series, Apr.

(List continued on next page.)

OTHER PUBLICATIONS 17-30, 1988, Invited Speaker, Keystone, Colorado.

Carney et al., Novel Monoclonal Antibodies for the Specific Detection of the Harvey and N Ras p21s, Cold Spring Harbor Laboratory Meeting, Sep. 1988.

Delellis et al., Monoclonal Antibodies to Ras Encoded p21 Proteins: A Biochemical and Immunohistochemical Analysis, International Academy of Pathology, Mar. 1987.

Ng et al., Production and Characterization of MAb Specific to Activated p21 Ras Protein with Aspartic Acid Substitution at Position 13, 4th Annual Oncogene Meeting, Frederick, Md., Jul. 1988.

Pullano et al., Monoclonal Antibody R256 Binds Activated Ras p21 Molecules with Arginine at position 12, 4th Annual Oncogene Meeting Frederick, Maryland, Jul. 1988.

Pullano et al., A Monoclonal Antibody Specific for an Activated Ras p21 with Arginine at Amino Acid 12, Federatiion of American Societies for Experimental Biology, 72nd Annual Meeting, May 1-5, 1988, Las Vegas, Nevada.

Rabin et al., Expression of Ras and NEU Oncogene Proteins as Determined by Monoclonal Antibodies, Cold Spring Harbor in Laboratory Meeting, Sep. 1988.

Trimpe et al., Flow Cytometric Analysis of c-erbB-2 and Ras Oncogene Products in Human Breast Carcinoma Cells, 11th Annual San Antonio Breast Cancer Symposium, Nov. 29-30, 1988.

Trimpe et al., Flow Cytometric Analysis of c-erbB and Ras Oncogene Products in Human Breast Carcinoma cells, Cold Spring Harbor Laboratory Meeting, Sep. 1988.

Trimpe et al., Flow Cytometric Analysis of Ras p21 in Transformed Cell Lines and Solid Tumors, American Association for Cancer Research, New Orleans, Louisiana, May 24-28, 1988 #5960.

Bos, Cancer Research, pp. 4682-4689, vol. 49 (Sep. 1, 1989).

Siddle, Alternative Immunoassays, pp. 26-30 (1985), W. P. Collins (ed.).

*Biotechnology*, Catalogue of Fisher Scientific, 1983 p. 97.

DETECTION, QUANTITATION AND CLASSIFICATION OF RAS PROTEINS IN BODY FLUIDS AND TISSUES

CROSS REFERENCE TO RELATED APPLICATION

This application is a continuation of U.S. Ser. No. 815,577, filed Dec. 27, 1991, now abandoned, which was a continuation of U.S. Ser. No. 334,823, filed Apr. 11, 1989, now abandoned, which was a continuation-in-part of U.S. Ser. No. 185,582, filed Apr. 22, 1988, now abandoned; and a continuation-in-part of U.S. Ser. No. 185,194, filed Apr. 22, 1988, now abandoned; and a continuation-in-part of U.S. Ser. No. 071,175, filed Jul. 8, 1987, now U.S. Pat. No. 5,081,230, issued Jan. 14, 1992; and a continuation-in-part of U.S. Ser. No. 158,730, filed Feb. 22, 1988, now U.S. Pat. No. 5,028,527, issued Jul. 2, 1991; and a continuation-in-part U.S. Ser. No. 111,315, filed Oct. 22, 1987, now U.S. Pat. No. 4,898,932, issued Feb. 6, 1990, a continuation-in-part U.S. Ser. No. 913,905, filed Oct. 1, 1986, now abandoned, and a continuation-in-part of U.S. Ser. No.696,197, filed Jan. 29, 1985, now abandoned.

FIELD OF THE INVENTION

This invention relates to the detection, quantitation and classification of ras p21 proteins in body tissues or body fluids and, more particularly, to the detection and quantitation of total cellular ras including normal and mutated ras proteins, as well as, identifying and quantitating total cellular ras p21 proteins into individual components such as normal ras, mutated ras, and the individual Harvey, Kitsten and N ras protein families.

BACKGROUND OF THE INVENTION

Harvey, Kirsten and N ras proteins are immunologically related proteins and are collectively termed p21. They are products of the ras family of cellular genes which are found in a wide variety of nucleated mammalian cells. The ras genes appear to be frequent targets of genetic alterations that can lead normal cells along the pathway to malignancy. Ras oncogenes have been identified in a wide array of premalignant and malignant cells.

The p21 proteins consist of about 188-189 amino acids having a molecular weight of about 21,000 daltons. Viral and cellular ras genes encode membrane bound proteins (Willingham et al., Cell 19;1005 (1980)) which bind guanine nucleotides (Schlonick et al., PNAS (USA) 76:5355 (1979); Papageorge et al., J. Virol. 44:509 (1982); and Fine et al., Cell 37:151 (1984)) and possess intrinsic GTPase activity (McGrath et al., Nature 301:644 (1984); Sweet et al., Nature 311:273 (1984); Gibbs et al., PNAS (USA) 81:5704 (1984); and Manne et al., PNAS 82:376 (1985)).

DNA mediated transfection experiments using NIH3T3 cells as recipients have led to the identification of a family of activated transforming genes homologous to the ras genes of the Harvey (Ha-ras) and Kirsten (Ki-ras) sarcoma viruses. A third member of the ras family designated N-ras has been identified but has not been found to have a retroviral counterpart. Activated (mutated) ras genes are structurally distinct from their normal homologs, having amino acid substitutions in the protein at positions 12, 13, or 61. (Tabin et al., Nature 300:143 (1982); Reddy et al., Nature 300:149 (1982); Bos et al., Nature 315:716 (1985); Yuasa et al., Nature, 303:775-779 (1983); Der et al., Cell 44:167-176 (Jan. 17, 1986)). Taparowsky et al., Banbury Report, 14:123-133 (1983) cited in Chem. Abstracts CA 100(1):1425n, teaches that the change at residue 12 from N-terminus of the H ras p21 from glycine to valine is sufficient to convert the normal protein to a transforming protein.

Shimizu et al., Nature 304:497-500 (1983) cited in Chem. Abstracts 99(19):1530936, teaches the presence of a cysteine residue at amino acid 12 in the human lung cancer cell line calu-1 homolog of the v-Ki-ras gene. Fasano et al., J. Mol. Appl. Genet., 2(2):173-180, cited in Chem. Abstracts CA 99(19):153080v, teaches that the T24 H-ras-1 gene product is nearly identical to the v-H-ras p21 transforming protein encoded by Harvey sarcoma virus. Recent reports have shown the presence of activated ras p21 proteins in 40-50% of human colorectal cancers and preneoplastic lesions of the colon termed adenomas (Bos et al., Nature 327:293 (1987), Forrester et al., Nature 327:299 (1987) and Volgelstein et al., NEJM 319:525 (September 1988)). Recent studies have also shown expression of activated ras genes and mutated ras p21 proteins in 20-30% of lung carcinomas (Rodenhuis et al., Cancer Res., 48:5738 (1988)) and over 90% of pancreatic carcinomas (Almoguera et al., Cell 53:549 (1988)). In certain forms of leukemia such as acute myelogeneous leukemia and in certain preleukemic states, activated ras p21 proteins have been described.

These activated ras genes and mutated proteins have also been found in established cell lines as well as primary and metastatic tumors. Gambke et al., (Nature 307:476, 1984), demonstrated a transforming N-ras gene in bone marrow cells from a patient with acute myeloblastic leukemia (AML). In contrast, DNA from fibroblast cells from the same patient was not transforming.

The p21 ras protein in its normal nonactivated form contains the glycine amino acid at positions 12 and 13 and the glutamine amino acid at position 61. The p21 protein found in normal cells has the following primary amino acid structure for the amino acid sequence 5 to 19: [5]Lysine-leucine-valine-valine-valine-glycine-alanine-glycine-glycine-valine-glycine-lysine-serine-alanine-leucine[19].

Previous reports have described several rat monoclonal antibodies reactive with normal and activated or oncogenic (mutated) ras p21 proteins in yeast and mammalian cells. (Robinson et al., Br. J. Cancer 54:87783-883 (1986), Furth et al., J. Virol. 43:294 (1982)).

EPO Patent Application No. 85111824.0 published on, Apr. 16, 1986, and European Patent Application No. 85111823.2 published on Mar. 26, 1986, disclose a polypeptide consisting of amino acids 5 to 17 of the ras p21 protein containing a cysteine residue inserted between positions 16 and 17 and further containing amino acid substitutions at position 12. Amino acids valine, serine, arginine, cysteine, aspartic acid or alanine were inserted at position 12. These polypeptides were coupled to carrier proteins and used as immunogens to induce the production of antibodies discussed therein. This reference further indicates that antibodies capable of distinguishing ras oncogenes from their normal counterparts by virtue of single amino acid differences in the p21 gene product may be applicable to diagnostic detection of malignant cells in clinical situations and it further indicates that such antibodies capable of distinguishing normal ras p21 from mutant ras p21 having a single amino acid difference at position 12 or 61 "would be used to detect the ras oncogene product by standard techniques such as immunofluorescence, immunoperoxidase staining, immunoprecipitation, ELISA, or Western blotting techniques."

Carney et al., PNAS (USA) 83:7485–7489 (1986) and EPO Publication No. 019003 published on Aug. 6, 1986, disclose a monoclonal antibody specific for an activated ras protein. This monoclonal antibody was raised against a synthetic peptide corresponding to amino acids of a mutated ras gene encoding valine instead of glycine at position 12. EPO Publication No. 019003 mentions that monoclonal antibody DWP is useful in the diagnosis of primary and metastatic lesions by conventional diagnostic methods and that diagnosis can also be carried out by conventional in vitro diagnostic procedures such as the assay of human blood samples or other bodily fluids. Carney et al., UCLA Symp. Mol. Cell. Biol., New Ser. 1985 cited in Chem. Abstracts, CA 104:1665706, disclose a monoclonal antibody raised against a ras related synthetic peptide showing immunoreactivity with human carcinomas. Carney et al. reported a series of monoclonal antibodies raised against synthetic peptides containing amino acid substitutions of glutamic acid, arginine or valine at position 12 (A Book of Abstracts from the 3d Annual Meeting on Oncogenes held at Hood College, Frederick, M.D., Jul. 7–11, 1987). Other monoclonal antibodies generated by various methods have also been reported to react with the various forms of the ras p21 protein. Hand et al., Proc. Nat. Acad. Sci. USA, Vol. 81, pp. 5227–5231 (1984); Thor et al., Nature, Vol. 311, pp. 562–565 (1984); Wong et al., Cancer Research, Vol. 46, pp. 6029–6033 (1986); and Tanaka, Proc. Natl. Acad. Sci. USA, Vol. 82, pp. 3400–3404 (1985).

Several scientific reports have shown that normal cells contain ras proteins with glycine at position 13.

In 1985 Bos et al. (Nature 315:726 1985) demonstrated that DNA isolated from cells of AML patients were able to transform NIH3T3 cells. This result is indicative and highly suggestive for the presence of an oncogene. These transforming genes were shown to be activated ras genes. In contrast, DNA from normal tissues were non-transforming and therefore did not contain activated N ras. These investigators analyzed the activated N ras genes for the presence of mutations using oligonucleotide probes and found that the activated N ras genes contain mutations that result in amino acid substitutions at position 13 of the protein. These mutations at position 13 were shown to be either aspartic acid or valine instead of the normal amino acid glycine.

Two reports in 1987 described ras mutations with arginine at position 13. Nitta et al. have shown (Jpn. J. Cancer Res. (Gann), 78:21–26 1987) an amino acid substitution of arginine for glycine at position 13 of an activated N ras p21 isolated from a human rectal carcinoma. A report by Hirai et al. (Nature 327:430 1987) has shown activated N ras genes in bone marrow cells from patients with myelodysplastic syndrome. The observations made by Hirai et al. suggest that the presence of activated N ras genes with position 13 mutations may be important in early stages of leukemia.

A report by E. Liu et al. (Nature 330:186, 1987) demonstrated the presence of the aspartic acid mutation at position 13 of the ras p21 in a patient with myelodysplastic disease 1.5 years before the patient progressed to acute leukemia. Thus screening patients with myelodysplastic syndrome for the presence of activated ras proteins with position 13 mutations with monoclonal antibodies may be a valuable test to predict which patients with myelodysplastic syndrome have an increased risk of developing acute leukemia.

Most recently, Wodnar-Filipowicz et al. reported (Oncogene, pp. 457–461, Vol. 1, No. 4 (1987)) the presence of activated N ras genes in a human T cell non-Hodgkin's lymphoma. These studies demonstrated the substitution of cysteine for glycine at position 13.

Reports have suggested that the 188–189 amino acid sequence of the H, Ki, and N ras p21s have been greatly conserved throughout evolution. However, the most significant differences between the H, Ki, and N p21 proteins appear to be localized in a segment having 15–20 amino acids located at the carboxy end of the p21 protein (Taparowsky et al., Nature 300:762 (1982)).

Furthermore, McGrath et al., Nature 304:501–506 (1983), and Shimizu et al., Nature 304:497–500 (1983), have shown that the Ki gene has the capacity to encode two distinct proteins referred to as Ki4A and Ki4B. The terms Ki4A and Ki4B are used interchangeably with Ki2A and Ki2B. Since this variable region exists among amino acids 160–180 at the C-terminal end of the ras p21, then it is theoretically possible to generate monoclonal antibodies that could specifically bind the individual H, Ki4A, Ki4B, and N ras p21s. Since reports indicate that activation of a particular ras gene such as the N ras gene in acute myelogenous leukemia (Bos et al., Nature 315:726 (1985)) or the overexpression of the particular H-ras gene (Spandidos et al., Anticancer Res. 4:269 (1984)) is frequently associated with a specific type of cancer (breast cancer).

European Patent Application No. 86107244.5, published on Dec. 3, 1986, discloses polypeptides having amino acid sequences derived from the variable regions of ras$^H$, ras$^N$, ras$^{4KA}$ and ras$^{4KB}$ protein families, immunogenic compositions wherein these polypeptides are covalently attached to immunogenic carriers, antibodies produced from such immunogens wherein these antibodies are specific for the ras oncogene from which the polypeptide sequence was derived and immunoassays employing these antibodies to distinguish among the individual p21 ras oncogene families. The peptide structures disclosed correspond to amino acids 171–189 and 170–189 of p21 H ras, 170–186 of p21 N ras, 171–186 of p21 Ki4A ras, and 170–185 of p21 Ki4B ras. It appears that no antibodies were deposited.

U.S. Pat. 4,535,058, issued Aug. 13, 1985 to Weinberg et al., discloses the general concept of using hybridoma technology to produce monoclonal antibodies to altered forms of ras p21 proteins or peptides encompassing position 12 of the proteins. In particular, attention is invited to column 4, lines 6–15, column 12, line 33 through column 13, line 29, and column 14, line 40 through column 16, line 22.

U.S. Pat. 4,699,877, issued Oct. 13, 1987 to Cline et al., discloses methods and compositions for detecting human tumors. A series of oligopeptides corresponding to antigenic regions in the peptide expression products of RNA present in retrovirus oncogenes is disclosed in column 5 at lines 17–60. Included in this series are Ras$^{Ki}$ and Ras$^{Ha}$ oligopeptides. This reference further discloses that these haptenic oligopeptides be used to induce antibody formation by coupling to an appropriate carrier. The method disclosed looks to cellular products such as mRNA or its expression product as diagnostic of the probable presence of malignant cells.

Tanaka et al., PNAS 82:3400 (1985), reported the generation of a series of rabbit sera to a variety of synthetic peptides corresponding to various portions of the ras p21s. Tanaka et al. reported the production of rabbit sera to a peptide corresponding to amino acids 160-179 of the v-Ha-ras. The anti-p21 sera was prepared by affinity purifying the rabbit sera and evaluating their specificity by biochemical assays. The specificity of these reagents, however, is questionable.

Srivastava et al., Molecular and Cellular Biology 5(11):3316 (1985), reported a series of rabbit polyclonal sera to synthetic peptides corresponding to various segments of the protein and in particular a segment corresponding to amino acid 161-176 of the H ras p21.

Tahara et al., Jpn. J. Cancer Res. (Gann) 77:517-522 (1986), disclose that a sheep anti-p21 antibody was generated against a synthetic peptide corresponding to positions 160-179 of the v-Ha-p21.

Bizub et al., Oncogene 1:131-142 (1987), raised antisera in mice, rats and rabbits to a variety of peptides in the H, Ki and N ras variable regions. Some of the polyclonal antibodies described in this report were affinity purified rabbit sera raised against peptides corresponding to amino acids 171-189 of the H p21 or to peptides corresponding to amino acids 171-186 of the Ki4B p21. According to this report, additional antibodies to the ras p21s are available at the N.C.I. repository (Microbiological Assoc. Inc., Bethesda, Md.). The antisera mentioned in the Bizub et al. report indicated that antibodies available at the N.C.I. were raised against a peptide structure correlating to the amino acid sequence 157-180 of the ras p21s.

Hand et al., JNCI, 79(1):59-65 (July 1987) disclose direct-binding liquid competition assays using monoclonal antibody Y13-259 and immunohistochemical assays in concert with cDNA probes for identification of specific ras point-mutated oncogenes or proto-oncogenes may be a possible means to quantitate ras p21 in human carcinomas and benign lesions. Monoclonal antibody Y13-259 discussed in Furth et al., J. Virol. 43:294-304 (1982) is a rat monoclonal generated against the native form of v-Ha-ras p21.

Similarly, Ohuchi et al., Cancer Research 47:1413-1420 (Mar. 1, 1987) disclose enhanced expression of c-Ha-ras p21 in human stomach adenocarcinomas defined by immunoassays using monoclonal antibodies and in situ hybridization. Specificity of the monoclonal antibodies used is questionable.

Caruso et al., Int. J. Cancer 38:587-595 (1986), disclose quantitative analysis of ras p21 in mammalian cells using monoclonal antibodies Y13-259 as discussed above and Y13-238, a rat monoclonal which selectively immunoprecipitate the Ha-MuSV-encoded ras p21.

Niman et al., PNAS (USA) 82:7924-7928 (1985), disclose the use of anti-peptide antibodies to detect oncogene-related proteins in urine. Increased levels of oncogene-related proteins were found during neoplasia and pregnancy. The peptide fragments were selected because they represented highly conserved regions of their oncogene families—sis, ras, and fes. The ras peptide was the Ha ras sequence located 37-59 amino acids downstream from the threonine residue autophosphorylated by p21 encoded by v-Ha-ras or v-Ki-ras. Detection of a 21,000 dalton protein was reported. However, it is not clear whether this protein was a ras related protein due to the questionable specificity of the reagents used.

PCT Application having International Publication Number WO 85/00807, published on Feb. 28, 1985, describes the production of polypeptide-induced monoclonal antibodies to oncoproteins and their use in diagnostic systems to assay for the presence of an oncoprotein.

SUMMARY OF THE INVENTION

The subject of this invention is an immunoassay for detecting, quantitating or classifying total cellular ras p21, activated ras p21, or individual Harvey, Kirsten, or N-ras families of ras proteins in bodily fluids, tissues, or cells comprising:

(a) reacting the bodily fluids, tissues, or cells suspected to have ras p21 proteins with an immobilized ras p21 capture reagent, said reagent being at least one antibody selected from the group consisting of (i) anti-p21 pan reactive antibodies, (ii) monoclonal antibodies which specifically bind to an epitope of an activated ras protein having an amino acid substitution of arginine, glutamic acid, aspartic acid, serine, or cysteine at position 12 and do not bind to an epitope containing glycine at position 12, (iii) monoclonal antibodies which specifically bind to an epitope of an activated ras protein having an amino acid substitution of aspartic acid or valine at position 13 and do not bind to an epitope containing glycine at position 13, (iv) monoclonal antibodies which specifically bind to an epitope of an activated ras protein having an amino acid substitution of histidine, lysine, leucine or arginine at position 61 and do not bind to an epitope containing glutamine at position 61, (v) monoclonal antibodies reactive with Harvey ras proteins and not reactive with Kirsten 2A, 2B or N families of ras proteins, (vi) monoclonal antibodies reactive with N ras proteins and not reactive with Kirsten 2A, 2B or Harvey families of ras proteins, (vii) monoclonal antibodies reactive with Kirsten 2A ras proteins and not reactive with Kirsten 2B, N or Harvey families of ras proteins, (viii) monoclonal antibodies reactive with Kirsten 2B ras proteins and not reactive with Kirsten 2A, N or Harvey families of ras proteins, (b) reacting the product of step (a) with at least one detectably labeled antibody selected from the group consisting of (i) anti-p21 pan reactive monoclonal antibodies which when tested in a microtitre plate-based ELISA using the standard conditions described above, with 1 to 10 ng of the antibody per well, the antibody provides an optical density between about 1.5 and about 2.5, (ii) monoclonal antibodies which specifically bind to an epitope of an activated ras protein having an amino acid substitution of arginine, glutamic acid, aspartic acid, serine, or cysteine at position 12 and do not bind to an epitope containing glycine at position 12, (iii) monoclonal antibodies which specifically bind to an epitope of an activated ras protein having an amino acid substitution of aspartic acid or valine at position 13 and do not bind to an epitope containing glycine at position 13, (iv) monoclonal antibodies which specifically bind to an epitope of an activated ras protein having an amino acid substitution of histidine, lysine, leucine or arginine at position 61 and do not bind to an epitope containing glutamine at position 61, (v) monoclonal antibodies reactive with Harvey ras proteins and not reactive with Kirsten 2A, 2B or N families of ras proteins, (vi) monoclonal antibodies reactive with N ras proteins and not reactive with Kirsten 2A, 2B or Harvey families of ras proteins, (vii) monoclonal antibodies reactive with Kirsten 2A ras proteins and not reactive with Kirsten 2B, N or Harvey families of ras proteins, (viii) monoclonal antibodies reactive with Kirsten 2B ras proteins and not reactive with Kirsten 2A, N or Harvey families of ras proteins, and (c) detecting, quantitating or classifying the product of step (b).

DETAILED DESCRIPTION OF THE INVENTION

Figure 1:
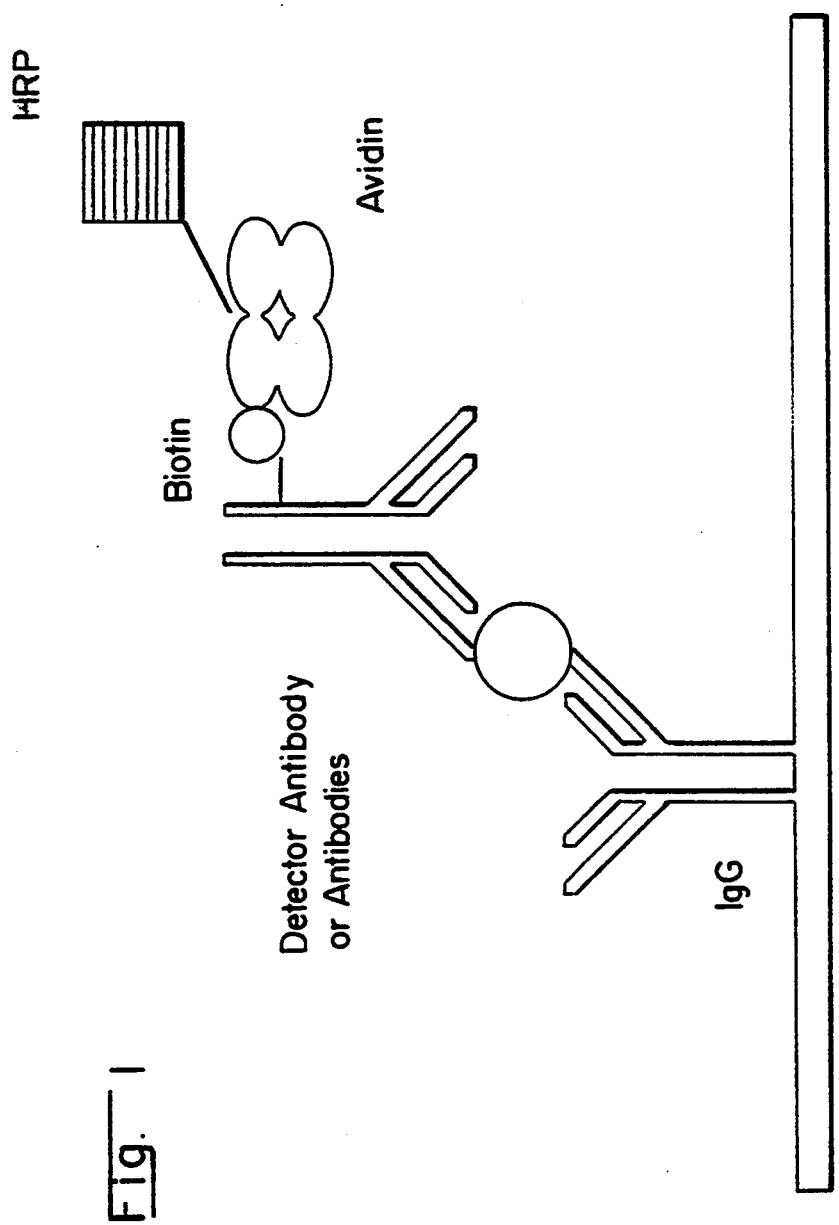
FIG. 1 is a diagram illustrating a forward sandwich immunoassay format.

This invention relates to the detection, quantitation, and classification of ras p21 proteins in cells, bodily tissues, bodily fluids, such as, blood, serum, plasma, urine, stool, saliva, or aspirates and bodily secretions, such as, sweat.

Surprisingly and unexpectedly, it has been found that normal p21, activated p21 or ras family specific p21 secreted or released by cells, p21 secreted or released by cells but bound to fragments of cell membranes, as well as cellular ras, can be detected and quantitated in bodily tissues and fluids using the immunoassay of the invention. This is surprising and unexpected because both viral and cellular ras proteins were believed to be localized to the inner face of the plasma membrane and because it is believed that no one heretofore has unequivocally demonstrated detection, quantitation, and classification of ras p21 proteins in bodily fluids.

The term total cellular ras means, collectively, cytoplasmic forms of p21, membrane bound forms of p21, and/or secreted forms of p21 which include (1) normal ras p21 proteins, (2) activated ras p21 proteins having an amino acid substitution of valine, arginine, glutamic acid, aspartic acid, cysteine, serine or alanine at position 12, (3) activated ras p21 proteins having an amino acid substitution of aspartic acid or valine at position 13, (4) activated ras p21 proteins having amino acid substitutions of lysine, leucine, histidine or arginine at position 61; and (5) family specific, Harvey, Kitsten, or N ras p21 proteins.

The abbreviations H and Ha are used interchangeably herein to designate the Harvey ras family. Similarly, the abbreviations K and Ki are used interchangeably to designate the Kirsten ras family and K2A and K2B are used interchangeably with K4A and K4B.

The terms oncogenic, activated and mutated are used interchangeably.

The terms immunoprecipitate and immunoconcentrate are used interchangeably.

The term antibody means polyclonal, monoclonal or an immunoreactive fragment thereof.

Antibodies which are suitable for practicing the instant invention include the following or equivalents thereof:

Polyclonal Antibodies

Polyclonal anti-p21 pan reactive antibodies which react with normal and activated forms of ras p21 proteins can be used to practice the invention. Techniques for producing polyclonal antibodies are well known to those skilled in the art. Such antibodies can be generated by immunizing rabbits or goats with an immunogen such as a purified cellular ras p21 protein or a recombinant ras p21 protein. For example, recombinant p21 proteins expressed in bacteria can be used. These recombinant proteins can have the normal or activated peptide structures. It has been found that a recombinant p21, having arginine at position 12, expressed in *E. coli.* works well. Techniques are also known for producing recombinant proteins. Described below is a synthesis of a recombinant p21 protein having arginine at position 12. Such synthesis is also described in Feig et al., Molecular Endocrinology, pages 127-136, Vol. 1, No. 2 (1987).

Synthesis of Recombinant Ras p21 Having Arginine at Position 12

A ras expression vector designated pXVR which directs the synthesis of an authentic viral Harvey ras p21 was constructed in the following manner:

A 720 base pair restriction fragment encoding all but the first five amino acids of the viral-Harvey ras gene was ligated by standard procedures to a 32 base pair synthetic oligomer containing a bacterial Shine-Delgarno sequence followed by a 6 base pair spacer plus the first five codons of the viral Harvey ras. To this material was ligated a plasmid backbone from pTR1340 containing a tac promoter as well as origin of replication and ampicillin resistance gene from pBR322.

The pXVR constructs were transformed into the *E. coli* strain PR13-Q which overproduces lac represser to partially repress the tac promoter and hence maintain cell viability.

In order to induce production of the p21, the *E. coli* cells are incubated with isopropylthio-B-D-galactoside (IPTG) which induced the synthesis of large amounts of p21.

More specifically, the *E. coli* cells are grown until there is an optical density (O.D.) reading of 0.25 at A590. P21 is induced by adding 5 Mm IPTG. After 1 hour, the *E. coli* cells are collected by centrifugation. The cell pellet is resuspended in lysis buffer (25 mM tris-HCl, 0.7 mM $Na_2HPO_4$, 5 mM KCl, 0.14M NaCl, 5 mM EDTA, 10 mM $MgCl_2$, 1% Triton X-100, 25% sucrose and 1 mg/ml lysozyme at pH 7.4, and vortexed. Material is frozen/thawed two times and the extract incubated with DNase and then centrifuged at 10,000×g for 15 minutes. The pellet is washed in 1% Triton X-100, resuspended in 50 µl 3.5M guanidine hydrochloride in 20 mM MES 2(N-morpholine ethane sulfonic acid), pH 7.0 and the particulate matter removed by centrifugation.

The following describes synthesis of a recombinant p21 having leucine at position 61 which can also be used to generated pan reactive polyclonal antibodies.

Synthesis of Recombinant Protein Having Leucine at Position 61

Using a full-length human ras-Harvey cDNA clone in an M13 vector, the appropriate codon 61 substitutions are introduced by in VitrQ mutagenesis as described in Der et al., Cell, pages 167–176, Vol. 44 (Jan. 17, 1986). In Vitro mutagenesis has been widely used to identify functional domains of proteins and to correlate biochemical and biological activities. A ras expression vector is constructed using the approach described above. This design is similar to the designs reported by J. P. McGrath, Nature 310:644, 1984 and J. C. Lacal, PNAS 81:5305, 1984, to produce intact ras protein in bacteria.

Monoclonal Antibodies

Hybridoma methodology and screening protocols are described in subsection (e) below. These methods are used to generate the antibodies described below by using the peptides described below coupled to a carrier protein. Screening protocols are tailored to screen for desired reactivity.

a) Anti-p21 Monoclonal Antibodies

Anti-p21 pan reactive monoclonal antibodies constitute the subject matter of a co-pending application filed on Jul. 8, 1987, having serial number 071,175 now U.S. Pat. No. 5,081,230, issued Jn. 14, 1992 and which is hereby incorporated by reference. The anti-p21 pan reactive monoclonal antibodies described therein were generated by using a recombinant Ha-ras p21 protein having an arginine amino acid at position 12 instead of glycine which is present in the normal Ha-ras p21 protein. Synthesis of the recombinant protein is described above. Hybridomas secreting these anti-p21 monoclonal antibodies were designated ras 8, ras 10 and ras 11. All of which were deposited in the American Type Tissue Culture Collection (ATCC) under the Budapest Treaty on May 12, 1987. Hybridoma ras 8 was designated HB 9428, Hybridoma ras 10 was designated HB 9426, and Hybridoma ras 11 was designated HB 9427.

These anti-p21 pan reactive monoclonal antibodies when tested in a microtitre plate based ELISA, under standard conditions described below, provided an optical density at 488 nm of between about 1.5 and about 2.5.

Standard ELISA Conditions:

The purpose of the ELISA described in this section is to test whether the anti-p21 monoclonal antibody reacts with normal and oncogenic ras p21 protein. 500 ng of recombinant normal or oncogenic human ras protein was coated per well; 0.1 to 1000 ng of the antibody or antibody fragment in 50 microliters per well of phosphate buffered saline (PBS) containing bovine serum albumin (BSA) as test sample; overnight incubation at 37° C. followed by BSA-PBS wash; 10 ng of goat anti-mouse IgG antibody conjugated to horseradish peroxidase in 50 microliters of BSA-PBS as detection reagent; 60 minute incubation at 37° C. followed by BSA-PBS wash; 50 microliters of o-phenylene diamine in PBS containing 0.15% hydrogen peroxide as substrate; 10 minute development, 50 microliters of 4.5M sulfuric acid as stop reagent; and determination of optical density (OD) at 488 nm.

In addition to ras 8, 10, and 11, there are four other anti-p21 pan reactive monoclonal antibodies which, when tested in a microtitre-based ELISA under the standard conditions described above, provide an optical density at 488 nm of between 1.5 and 2.5. These antibodies are ras 9, 13, 17, and 20. Ras 9, 13, and 17 were generated using the recombinant Harvey ras protein having arginine at position 12. The synthesis of this protein is described above. Ras 20 was generated using a recombinant Harvey ras protein having leucine at position 61 as the immunogen. The synthesis of this protein is also described above. Hybridoma cell lines Ras 9, 13, 17, and 20 were deposited with the ATCC under the terms of the Budapest Treaty on Mar. 29, 1989.

Ras 9 was accorded ATCC designation HB10058.
Ras 13 was accorded ATCC designation HB10057.
Ras 17 was accorded ATCC designation HB10054.
Ras 20 was accorded ATCC designation HB10059.

In addition to the immunoassay described herein, hybridoma cell lines Ras 9, 13, 17, and 20 can also be used to immunoblot and to immunoconcentrate ras p21 proteins.

b) Monoclonal Antibodies Reactive with Ras Proteins Mutated at Position 12

The monoclonal antibody designated DWP was disclosed in the European patent application referred to above, (EPO Publication No. 019003), specific for p21 mutated at position 12 by having a valine in place of glycine. This monoclonal antibody and monoclonal antibodies specific for p21s having glutamic acid or arginine mutations at position 12 constitute the subject matter of a copending application filed on Oct. 22, 1987, having serial number 111,315 now U.S. Pat. no. 4,878,932, issued Feb. 6, 1990 and which is hereby incorporated by reference. This application is a continuation in part of two earlier filed applications (U.S. Ser. No. 696,197 filed Jan. 29, 1985 now abandoned and U.S. Ser. No. 913,905 filed Oct. 1, 1986 now abandoned) and claims priority thereof. Hybridomas secreting monoclonal antibodies reactive with p21 proteins having valine, glutamic acid or arginine were deposited in the ATCC under the Budapest Treaty.

The hybridoma cell line secreting a monoclonal antibody reactive with mutated ras p21 proteins having valine at position 12 referred to as DWP was deposited on Jan. 23, 1989 and given ATCC designation number HB8698.

The hybridoma cell lines secreting monoclonal antibodies reactive with mutated ras p21 proteins having glutamic acid at position 12 were referred to as E184 and E170. Hybridoma E184 was deposited on Sep. 11, 1986 and was given ATCC designation number HB9194. Hybridoma E170 was deposited on Sep. 11, 1986 and was given ATCC designation number HB9195.

The hybridoma cell line secreting a monoclonal antibody reactive with mutated ras p21 proteins having arginine at position 12 referred to as R256 was deposited on Sep. 11, 1986 and was given ATCC designation number HB9196.

The monoclonal specific for the valine substitution was generated by using an immunogen containing the following polypeptide sequence: [5]lysine-leucine-valine-valine-valine-glycine-alanine-valine-glycine-valine-glycine-lysine[16].

The monoclonal specific for the glutamic acid substitution was generated by using an immunogen containing the following polypeptide sequence: [5]lysine-leucine-valine-valine-valine-glycine-alanine-glutamic acid-glycine-valine-glycine-lysine[16].

The monoclonal specific for the arginine substitution was generated by using an immunogen containing the following polypeptide sequence: [5]lysine-leucine-valine-valine-valine-glycine-alanine-arginine-glycine-valine-glycine-lysine[16].

Other monoclonal antibodies which can be used in the assay of this invention include monoclonal antibodies which specifically bind to an epitope of an activated ras p21 protein having aspartic acid at position 12 and do not bind to an epitope having glycine at position 12.

Monoclonal antibodies reactive with mutated ras p21 proteins having aspartic acid at position 12 were produced by hybridoma cell lines D113, D205, and D210. These cell lines were deposited with the ATCC under the Budapest Treaty. Hybridoma cell line D113 was deposited on Mar. 31, 1989 and was accorded ATCC designation number HB10086. Hybridoma cell line D205 was deposited on Mar. 29, 1989 and was accorded ATCC designation number HB10061. Hybridoma cell line D210 was deposited on Mar. 31, 1989 and was accorded ATCC designation number HB10083.

Hybridoma cell lines D113, D205, and D210 were produced using the the dodecapeptide [5]lysine-leucine-valine-valine-valine-glycine-alanine-aspartic acid-glycine-valine-glycine-lysine[16] to immunize mice according to the procedure described below. As was stated above, hybridoma methodology and screening protocols are also described below. The monoclonal antibodies were screened for their reactivity with the peptide containing aspartic acid at position 12 and for lack of reactivity with peptide containing glycine at position 12, i.e., aspartic acid positive, glycine negative.

Monoclonal antibodies which can be used in the immunoassay of this invention also include monoclonal antibodies which specifically bind to an epitope of an activated ras p21 protein having serine or cysteine at position 12 and do not bind to an epitope having glycine at position 12.

Monoclonal antibodies reactive with mutated ras p21 proteins having serine at position 12 were produced by hybridoma cell line S1107-8.3. This cell line was deposited with the ATCC under the Budapest Treaty on Mar. 29, 1989. Hybridoma cell line S1107-8.3 was accorded ATCC designation number HB10060.

Hybridoma cell line S1107-8.3 was produced using the the dodecapeptide [5]lysine-leucine-valine-valine-valine-glycine-alanine-serine-glycine-valine-glycinelysine[16] to immunize mice according to the procedure described below. Hybridoma methodology and screening protocols are also described below. The monoclonal antibodies were screened also for their reactivity with the peptides of interest, i.e., serine positive, glycine negative.

Monoclonal antibodies reactive with mutated ras p21 proteins having cysteine at position 12 were produced by hybridoma cell lines C-1119-9 and C-1119-10. These cell lines were deposited with the ATCC under the Budapest Treaty on Mar. 31, 1989. C-1119-10 was accorded ATCC designation number HB10088. C-1119-9 was accorded ATCC designation number HB10084.

Hybridoma cell lines C1119-9 and C1119-10 were produced using the the dodecapeptide [5]lysine-leucine-valine-valine-valine-glycine-alanine-cysteine-glycine-valine-glycine-lysine[16] to immunize mice according to the procedure described below. Hybridoma methodology and screening protocols are also described below. The monoclonal antibodies were screened also for their reactivity with the peptides of interest, i.e., cysteine positive, glycine negative.

c) Monoclonal Antibodies Reactive with Ras Proteins Mutated at Position 13

Also within the scope of this application are the monoclonal antibodies discussed in copending application filed on Feb. 22, 1988, having Ser. No. 158,730 now U.S. Pat. No. 5,028,527, issued Jul. 2, 1991 and which is hereby incorporated by reference. The monoclonals discussed therein are reactive with ras p21 proteins having an amino acid substitution at position 13. Specifically, aspartic acid and valine were substituted at position 13 in place of glycine which is normally present.

The monoclonal antibodies specific for the aspartic acid substitution were generated by using an immunogen containing the following polypeptide sequence: cysteine-[5]lysine-leucine-valine-valine-valine-glycine-alanine-glycine-aspartic acid-valine-glycine-lysine-serine-alanine-leucine[19]. The hybridomas secreting these monoclonal antibodies were designated D753-13(129) and D765-13 (146). These hybridomas were deposited in the ATCC under the Budapest Treaty on Jan. 29, 1988. Hybridoma D753-13(129) was accorded ATCC designation number HB9632. Hybridoma D765-13(146) was accorded ATCC designation number HB9633.

The monoclonal specific for the valine substitution was generated by using an immunogen containing the following polypeptide sequence: cysteine-[5]lysine-leucine-valine-valine-valine-glycine-alanine-glycine-valine-valine-glycine-lysine-serine-alanine-leucine[19].

The hybridoma secreting this monoclonal was designated V647-13. This hybridoma was deposited with the ATCC under the Budapest Treaty and was accorded ATCC designation number HB9634.

Other monoclonal antibodies reactive with ras proteins mutated at position 13 include monoclonal antibodies which specifically bind to an epitope of an activated ras p21 protein having arginine at position 13 and does not bind to an epitope having glycine at position 13.

These monoclonal antibodies can be generated by immunizing mice with an immunogen containing the following polypeptide sequence: [5]lysine-leucine-valinevaline-valine-glycine-alanine-glycine-arginine-valine-glycine-lysine[16] according to the procedure described below. Hybridoma methodology and screening protocols are also described below. The monoclonal antibodies are screened also for their reactivity with the peptides of interest, i.e., arginine positive (position 13), glycine negative (position 13).

d) Monoclonal Antibodies Reactive with Ras Proteins Mutated At Position 61

Monoclonal antibodies which specifically bind to an epitope of ras p21 protein having arginine, leucine, or histidine at position 61 and do not bind to an epitope having glutamine at position 61 were deposited with the ATCC under the Budapest Treaty.

The hybridoma cell lines producing monoclonal antibodies reactive with mutated ras p21 proteins having arginine at position 61 were produced by hybridoma cell lines R61-1, R61-2, R61-3, and R61-4. Hybridoma cell line R61-1 was deposited on Mar. 29, 1989 and was accorded ATCC designation number HB10063.

Hybridoma cell line R61-2 was deposited on Mar. 30, 1989 and was accorded ATCC designation number HB10069.

Hybridoma cell line R61-3 was deposited on Mar. 30, 1989 and was accorded ATCC designation number HB10071.

Hybridoma cell line R61-4 was deposited on Mar. 29, 1989 and was accorded ATCC designation number HB10062.

Hybridoma cell lines R61-1, R61-2, R61-3, and R61-4 were produced using an 11 mer peptide (undecapeptide) having the following structure: $^{57}$aspartic acid-threonine-alanine-glycine-arginine-glutamic acid-glutamic acid-tyrosine-serine-alanine$^{66}$-tyrosine to immunize mice according to the procedure described below. The terminal tyrosine residue was added to facilitate coupling to a carrier protein. Hybridoma methodology and screening protocols are also described below. The monoclonal antibodies were screened also for their reactivity with the peptides of interest, arginine positive (position 61), glutamine negative (position 61).

Monoclonal antibodies reactive with mutated ras p21 proteins having leucine at position 61 were produced by hybridoma cell lines L61-2 and L61-1. Hybridoma cell line L61-2 was accorded ATCC designation number HB10073. Hybridoma cell line L61-1 was accorded ATCC designation number HB10068. Both cell lines were deposited on Mar. 30, 1989.

Hybridoma cell lines L61-1 and L61-2 were produced using the 11 mer peptide (undecapeptide) having the following structure: $^{57}$aspartic acid-threonine-alanine-glycine-leucine-glutamic acid-glutamic acid-tyrosne-serine-alanine$^{66}$-tyrosine to immunize mice according to the procedure described below. Hybridoma methodology and screening protocols are also described below. The monoclonal antibodies were screened also for their reactivity with the peptides of interest, leucine positive (position 61), glutamine negative (position 61).

Monoclonal antibodies reactive with mutated ras p21 proteins having histidine at position 61 were produced by hybridoma cell lines H61-1, H61-2, H61-3, H61-4, and H61-5. Hybridoma cell line H61-1 was deposited on Mar. 30, 1989 and was accorded ATCC designation number HB10070. Hybridoma cell line H61-2 was deposited on Mar. 30, 1989 and was accorded ATCC designation number HB10092. Hybridoma cell line H61-3 was deposited on Mar. 30, 1989 and was accorded ATCC designation number HB10089. Hybridoma cell line H61-4 was deposited on Mar. 30, 1989 and was accorded ATCC designation number HB10087. Hybridoma cell line H61-5 was deposited on Mar. 30, 1989 and was accorded ATCC designation number HB10090.

Hybridoma cell lines H61-1, H61-2, H61-3, H61-4, and H61-5 were produced using the 11 mer peptide (undecapeptide) having the following structure: $^{57}$aspartic acid-threonine-alanine-glycine-histidine-glutamic acid-glutamic acid-tyrosine-serine-alanine$^{66}$-tyrosine to immunize mice according to the procedure described below. Hybridoma methodology and screening protocols are also described below. The monoclonal antibodies were screened also for their reactivity with the peptides of interest, histidine positive (position 61), glutamine negative (position 61).

Monoclonal antibodies reactive with mutated ras p21 proteins having lysine at position 61 are produced by a hybridoma cell line which is generated using an 11 mer peptide (undecapeptide) having the following structure: $^{57}$aspartic acid-threonine-alanine-glycine-lysine-glutamic acid-glutamic acid-tyrosine-serine-alanine$^{66}$-tyrosine. Mice are immunized according to the procedure described below. Hybridoma methodology and screening protocols are also described below. The monoclonal antibodies are screened also for their reactivity with the peptides of interest, lysine positive (position 61), glutamine negative (position 61).

e) Monoclonal Antibodies Reactive with Ras Proteins of the Individual Harvey, N and Kirsten Ras Families Monoclonals specific for Ha, N or Ki2A, Ki2B ras p21s are discussed in co-pending application filed on Apr. 22, 1988, having serial number U.S. Ser. No. 07/185,194 now abandoned and which is hereby incorporated by reference and which was filed simultaneously with U.S. Ser. No. 07/185,582 now abandoned. These monoclonals are also discussed in a co-pending application being filed simultaneously herewith having U.S. Ser. No. 07/334,822 filed Apr. 17, 1998, now abandoned. The monoclonal antibodies discussed therein can differentiate among the individual Ha-, N- and Ki-ras families.

The hybridomas producing monoclonals specific for H-ras were designated H-770-1.1.4, H-784-4.7.7 and H-873-3.5.3 and were deposited in the ATCC under the Budapest Treaty on Mar. 25, 1988. Hybridoma H-770-1.1.4 was accorded ATCC designation number HB9673. Hybridoma H-784-4.7.7 was accorded ATCC designation number HB9675. Hybridoma H-873-3.5.3 was accorded ATCC designation number HB9674.

The hybridomas producing monoclonals specific for N-ras were designated N-821-1.1.9 and N-838-1.1.6 and were deposited in the ATCC under the Budapest Treaty on Mar. 25, 1988. Hybridoma N-821-1.1.9 was accorded ATCC designation number HB9671. Hybridoma N-838-1.1.6 was accorded ATCC designation number HB9672.

The hybridoma cell lines producing monoclonals specific for Ki2A ras have been designated K2A-1 and K2A-2 and were deposited in the ATCC under the Budapest Treaty on Mar. 30, 1989. K2A-1 was accorded ATCC designation number HB10072. K2A-1 was accorded ATCC designation number HB10065.

The hybridoma cell lines producing monoclonal antibodies specific for Ki2B ras have been designated K2B-1, K2B-2, K2B-3, K2B-4, K2B-5, K2B-6, and K2B-7 and were deposited in the ATCC under the Budapest Treaty. K2B-1 was deposited on Mar. 30, 1989 and was accorded ATCC designation number HB10064. K2B-2 was deposited on Mar. 29, 1989 and was accorded ATCC designation number HB10055. K2B-3 was deposited on Mar. 30, 1989 and was accorded ATCC designation number HB10066. K2B-4 was deposited on Mar. 31, 1989 and was accorded ATCC designation number HB10085. K2B-5 was deposited on Mar. 29, 1989 and was accorded ATCC designation number HB10056. K2B-6 was deposited on Mar. 30, 1989 and was accorded ATCC designation number HB10067. K2B-7 was deposited on Mar. 31, 1989 and was accorded ATCC designation number HB10091.

Immunizations

In the case of Mab H-770-1.1.4, Balb/c×C57B1/6 mouse #4607 was immunized with the H-specific peptide coupled to carrier protein Keyhole Limpet Hemacyanin (KLH) via the glutaraldehyde method of A. Kagan et al., Methods of Hormone Radioimmunoassay, pp. 327–339 (2d Ed.)(1979). Unless stated otherwise, the Kagan method is the preferred method for all coupling/conjugation discussed herein. The H-specific peptide was composed of 18 amino acids corresponding to positions 163–180 of the ras H p21. The structure of the immunizing peptide was as follows: $^{163}$Isoleucine-arginine-glutamine-histidine-lysine-leucine-arginine-lysine-leucine-asparagine-proline-proline-aspartic acid-glutamic acid-serine-glycine-proline-glycine$^{180}$.

In the case of Mab H-784-4.7.7, Balb/c×C57B1/6 mouse #4615 was immunized with the H-specific peptide coupled to carrier protein KLH.

In the case of Mab H-873-3.5.3, Balb/c×C57B1/6 mouse #4606 was immunized with the H-specific peptide coupled to carrier protein KLH.

In the case of Mab N-821-1.1.9, Balb/c×C57B1/6 mouse #4486 was immunized with the N-specific peptide coupled to carrier protein Bovine Thyroglobulin (BTG) as discussed above.

In the case of Mab N-838-1.1.6, Balb/c×C57B1/6 mouse #4480 was immunized with the N-specific peptide coupled to BTG. The N-specific peptide was composed of 18 amino acids corresponding to positions 163–180 of the N ras p21. The structure of the N ras peptide was as follows: $^{163}$Isoleucine-arginine-glutamine-tyrosine-arginine-methionine-lysine-lysine-leucine-asparagine-serine-serine-aspartic acid-aspartic acid-glycine-threonine-glutamic acid-glycine$^{180}$.

The immunizing N and H-specific peptides were coupled to carrier proteins KLH and BTG respectively to enhance immunogenicity of the peptide. The first inoculation consisted of the peptide-carrier conjugate mixed with Complete Freunds Adjuvant. Total protein inoculated was 500 micrograms. Subsequent inoculations were given at two-week intervals. Three days before fusion mice were given an intraperitoneal inoculation of the appropriate immunogen.

In the case of Mabs K2A-1 and K2A-2, Balb/c×C57B1/6 some mice were immunized with a peptide corresponding to amino acids 163–180. Once again, peptides were coupled to carrier proteins prior to inoculations.

The peptide corresponding to amino acids 163–180 was composed of 18 amino acids and had the following structure: $^{163}$Isoleucine-arginine-glutamine-tyrosine-arginine-leucine-lysine-lysine-isoleucine-serine-serine-glutamic acid-glutamic acid-lysine-threonine-proline-glycine-cysteine$^{180}$.

Another peptide corresponding to amino acids 170–184 of Ki ras p21 can be used as an immunogen. It has the structure: $^{170}$lysine-isoleucine-serine-lysine-glutamic acid-glutamic acid-lysine-threonine-proline-glycine-cysteine-valine-lysine-isoleucine-lysine$^{184}$.

In the case of Mabs K2B-1, K2B-2, K2B-3, K2B-4, K2B-5, K2B-6, and K2B-7, Balb/c×C57B1/6 mice were immunized with peptides corresponding to amino acids 164–175. Peptides were again coupled to carrier proteins prior to inoculation.

The peptide corresponding to amino acid positions 164–175 of the Ki2B ras p21 was composed of 12 amino acids and has the following structure: $^{164}$arginine-lysine-histidine-lysine-glutamic acid-lysine-methionine-serine-lysine-aspartic acid-glycine-lysine$^{175}$.

Two other peptides corresponding to amino acids 163–180 and 168–183 of Ki2B ras p21 can also be used. They have the following structure: $^{163}$isoleucine-arginine-lysine-histidine-lysine-glutamic acid-lysine-methionine-serine-lysine-aspartic acid-glycine-lysine-lysine-lysine-lysine-lysine$^{180}$ and $^{168}$glutamic acid-lysine-methionine-serine-lysine-aspartic acid-glycine-lysine-lysine-lysine-lysine-lysine-serine-lysine-threonine$^{183}$.

The Ki2A and Ki2B-specific peptides were coupled to carrier proteins KLH or BTG to enhance immunogenicity of the peptide. The first inoculation consisted of the peptide carrier conjugate mixed with Complete Freunds Adjuvant. Total protein inoculated was 500 micrograms. Subsequent inoculations were given at two-week intervals. Three days before fusion mice were given an intraperitoneal inoculation of the appropriate immunogen.

Hybridoma Methodology

Three days after an intraperitoneal boost the spleens of the appropriate immune mice were removed and fused with the non-secretor myeloma cell Sp2/0. Spleen cell suspensions were prepared in serumless DMEM-high glucose medium and mixed with myeloma cells at a ratio of 4:1. This cell mixture was centrifuged at 1200×g for 10 minutes at room temperature. After removal of the supernatant, the cells were resuspended by gently tapping the tube. The fusion procedure was initiated by adding 1.0 ml of 45% w/v polyethylene glycol 3350 (Baker) at 37° C. over a 30-second period.

The cells were occasionally mixed with a pipette tip for 90 seconds and 5 ml of serumless DMEM-high glucose medium was added over a 3-minute period. This was followed by the addition of 14 ml of DMEM-high glucose supplemented with 10% fetal calf serum, L-glutamine, hypoxanthine, aminopterin and thymidine (referred to as HAT medium). The HAT medium was added over a 1-minute period.

Appropriate volumes of HAT medium were added to cells and then the cells were centrifuged at 800×g for 7 minutes at room temperature. Supernatants were aspirated and the cell pellet disrupted with 10 ml of HAT medium. Peritoneal cells from Balb/c×C57B1/6 were added and the final volume adjusted so that two hundred thousand spleen cells were dispensed to each well. Approximately 14 days later, tissue culture supernatants from wells containing hybridoma colonies were tested by ELISA for the desired reactivity with peptides conjugated to carrier proteins.

Screening Procedures and ELISA Protocol

For screening purposes, the H-specific peptide described above was conjugated to the BTG carrier protein while the N-specific peptide was conjugated to the KLH carrier protein. The rationale for coupling peptides to different carrier proteins for immunization and screening was to avoid selecting antibodies reactive with the carrier protein. The same rationale applied to the selection of carrier to conjugate to the Ki2A and Ki2B specific peptides.

Prior to screening hybridoma supernatants, 500 mg of the peptide-carrier conjugate was dispensed to 96 well microtiter plates for overnight incubation at 37° C. After incubation, plates were Hashed and unbound sites on the plates were blocked with bovine serum albumin (BSA).

At the time of screening hybridoma supernatants, 50 microliters of fluid was added to wells containing the appropriate peptide-carrier conjugate. Hybridoma supernatants were allowed to incubate overnight at 4° C. Supernatants were removed the next day and wells washed with the BSA solution. Each well subsequently received 50 microliters of goat anti-mouse IgG antibody conjugated to horseradish peroxidase (GAMHRP) diluted in BSA phosphate buffered saline (PBS). Wells were incubated for 60 minutes at 37° C. GAMHRP was removed after incubation and wells were washed three times with PBS-BSA mixtures. The presence of bound GAMHRP was determined by adding 50 microliters of the substrate o-phenylenediamine (OPD) in phosphate buffer containing 0.15% hydrogen peroxide. HRP, in combination with its substrate OPD, results in a yellow colored product. Development of the yellow product was allowed to occur at room temperature for 15 minutes. The enzymatic reaction was terminated by the addition of 50 microliters of 4.5% M sulfuric acid. Measurement of the resultant reaction product was accomplished by determining optical density at 488 nm on a Nunc Plate Reader (Nunc, Inc., Newbury Park, Calif.). Presence of the yellow color in the wells indicated that antibodies of interest were present in the hybridoma supernatants. The more antibody present in the culture fluid, the higher the optical density.

Using the above-described assay, Mabs H-770-1.1.4, H-784-4.7.7, and H-873-3.5.3 were found to be reactive with the H-specific peptide coupled to carrier protein and not reactive with the N, Ki2A and Ki2B-specific peptides also coupled to carrier protein. Mabs N-821-1.1.9 and N-838-1.1.6 were found to be reactive with the N ras specific peptide coupled to carrier protein and not reactive with the H, Ki2A and Ki2B-specific peptides coupled to carrier protein.

Mabs Ki2A-1 and Ki2A-2 were found to be reactive with the Ki2A specific peptide and not reactive with the H, N, and Ki2B specific peptides (amino acids 164–175) also coupled to carrier protein.

Mabs Ki2B-1, Ki2B-2, Ki2B-3, Ki2B-4, Ki2B-5, Ki2B-6, and Ki2B-7 were found to be reactive with the Ki2B specific peptide (amino acids 164–175) and not reactive with the H, N, and Ki2A peptides also coupled to carrier protein.

Specificity of Mabs for Peptides of Interest

In the next series of experiments, the anti-N and anti-H Mabs were tested for specificity with peptides not coupled to carrier proteins to ensure that the Mabs were specific for the peptides of interest and not reactive with the bond attaching the carrier protein to the peptide. Table 1 summarizes ELISA results of testing the anti-H and anti-N Mabs against the H, N, Ki2A and Ki2B specific peptides.

TABLE 1

| Hybridoma | H-Peptide | N-Peptide | Ki2A Peptide (AminoAcids 163–180) | Ki2B Peptide (AminoAcids 163–180) |
|---|---|---|---|---|
| H-770-1.1.4 | + | − | − | − |
| H-784-4.7.7 | + | − | − | − |
| H-873-3.5.3 | + | − | − | − |
| N-821-1.1.9 | − | + | − | − |
| N-838-1.1.6 | − | + | − | − |

These results show that Mabs raised against the H peptide were specific for that peptide and not with the N peptide, Ki2A peptide or with the Ki2B peptide. Results also demonstrate that the Mabs raised against the N peptide were specific for that peptide and not reactive or cross-reactive with the H ras related peptide, the Ki2A ras related peptide or with the Ki2B ras related peptide.

Similarly, Mabs for Ki2A and Ki2B are tested for specificity with peptides not coupled to carrier proteins to ensure that the Mabs are specific for the peptides of interest and not reactive with the bond attaching the carrier protein to the peptide. It is believed that Ki2A and Ki2B Mabs are specific for the peptides of interest and not reactive with the bond attaching the carrier protein to the peptide.

Reactivity and Specificity of the Anti-Peptide Mabs for Cellular ras Proteins

Immunoprecipitation and western blotting were used to determine whether the Mabs raised against the H and N ras peptides reacted with and were specific for the cellular H and N ras p21s. Experiments were performed using the following four cell lines:

1. Cell line designated 3T3-Hras (also designated PSV-13) overexpressed the H ras p21 protein.
2. Cell line designated 3T3-Nras overexpressed the N ras p21 protein.
3. Cell line (KNRK) designated 3T3-Ki2A expressed the viral form of the Ki p21 protein.
4. Cell line (SW480) designated 3T3-Ki2B expressed the cellular form of the Ki ras protein.

Nonradioactive extracts of the above-mentioned cells were incubated with an anti-H Mab, anti-N Mab, or an anti-p21 Mab designated Ras 10 for 1 hour. The Ras 10 anti-p21 Mab reacted with normal and oncogenic forms of the ras p21 proteins, as discussed above.

After incubation, a complex of rabbit anti-mouse Ig was added to protein A Sepharose for 30 minutes at 4° C. to capture the anti-H, anti-N, and anti-p21 Mabs.

After the 1 hour incubation, the samples were centrifuged and the resulting pellets washed. After the final wash, 50 microliters of a sodium dodecylsulfate reducing buffer was added to the pellet and heated for 5 minutes at 100° C. This material was then applied to a 12.5% polyacrylamide gel. Cellular proteins were separated according to molecular weight by running an electric current through the gel. After this electrophoresis procedure, the proteins were electrophoretically transferred to nitrocellulose membranes which had been blocked with PBS containing 5% BSA. The membranes were incubated for 1 hour with either an anti-p21 Mab ras 10 or mouse serum which served as a negative control. After incubation with Ras 10 or a negative control antibody, membranes were washed three times with PBS-NP-40. Membranes were then incubated with an anti-mouse immunoglobulin coupled to HRP for 1 hour to detect the mouse Mabs. Membranes were then washed three times with PBS-NP-40 and incubated with 4-chloro-1-naphthol substrate to complete the reaction. Experiments demonstrated that the anti-H Mabs were able to immuneprecipitate or capture the cellular H ras p21 from the 3T3-Hras cell line but did not react with cellular p21s from the N ras family, Ki2A family, or Ki2B family. Anti-N ras Mabs specifically immuneprecipitated or captured the cellular N ras p21 but did not react with the other cellular H, Ki2A, and Ki2B p21 protein families. The broadly reactive anti-p21 Mab Ras 10 reacted with p21 proteins from all the cells, whereas the negative control antibody did not react with any of the cellular ras p21s. These results are summarized below in Table 2.

TABLE 2

| Hybridoma | Cell Line | | | |
| --- | --- | --- | --- | --- |
| | PSV-13 | 3T3Nras | 3T3Ki2Aras | 3T3Ki2Bras |
| H-770-1.1.4 | + | − | − | − |
| H-784-4.7.7 | + | − | − | − |
| H-873-3.5.3 | + | − | − | − |
| N-821-1.1.9 | − | + | − | − |
| N-838-1.1.6 | − | + | − | − |
| Ras 10 | + | + | + | + |
| Negative Control (mouse serum) | − | − | − | − |

In a separate series of experiments the anti-H and anti-N Mabs were evaluated for their ability to detect the cellular H and N ras p21s without prior immuneprecipitation. To do this, cell extracts were applied directly to the 12.5% gel and electrophoresed to separate proteins. Proteins were transferred to nitrocellulose membranes and reacted with either the antiH, anti-N or the anti-p21 Mab Ras 10. The mouse antibodies were detected as described above. The results demonstrated that the anti-H Mabs reacted with only the cellular H ras p21s, whereas the anti-N Mabs reacted with only the cellular N ras p21s.

In accordance with this invention, the antibody or cocktail of antibodies discussed above which can be used for detection are detectably labeled with a reporter or with a member of a specific binding pair using conventional techniques.

Specific binding pairs can be of the immune or non-immune type. Immune specific binding pairs are exemplified by antigen-antibody systems of hapten/antihapten systems. There can be mentioned fluorescein/anti-fluoroscein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune pairs are biotin-streptavidin, intrinsic factor-vitamin B$_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxysuccinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethylaminopropyl)-carbodiimide (EDAC).

Homobifunctional crosslinkers, including the bifunctional imidoesters and bifunctional N-hydroxysuccinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The antibody, antibodies, or a member of the specific binding pair is coupled to the reporter which can be a radioactive isotope, enzyme, fluorogenic, chemiluminescent or electrochemical materials. Two commonly used radioactive isotopes are $^{125}$I and $^{3}$H. Standard radioactive isotopic labeling procedures include the chloramine T, lactoperoxidase and Bolton-Hunter methods for $^{125}$I and reduction methylation for $^{3}$H.

Enzymes suitable for use in this invention include, but are not limited to, horseradish peroxidase, alkaline phosphatase, B-galactosidase, glucose oxidase, luciferase, B-lactamase, urease and lysozyme. Enzyme labeling is facilitated by using dialdehyde, carbodiimide coupling, homobifunctional crosslinkers and heterobifunctional crosslinkers as described above for labeling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, Immunochemistry 8, 871 (1971), Avrameas and Ternynck, Immunochemistry 8, 1175 (1975), Ishikawa et al., J. Immunoassay 4 (3):209–327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably labeled with a reporter or with a first member of a specific binding pair. When the antibody is labeled with a first member of a specific binding pair, then detection is effected by reacting the antibody-first member of a specific binding complex with the second member of the binding pair which is labeled or unlabeled as mentioned above.

Moreover, the unlabeled detector antibody can be detected by reacting the unlabeled antibody with a labeled antibody specific for the unlabeled antibody. Such an anti-antibody can be labeled directly or indirectly using any of the approaches discussed above. For example, the anti-antibody can be labeled with biotin. The streptavidin-horseradish peroxidase system discussed above could then be used to facilitate detection.

One of the preferred embodiments of this invention utilizes biotin as the detectable label. The biotinylated antibody is in turn reacted with streptavidin-horseradish peroxidase complex. Orthophenylenediamine or 4-chloro-naphthol can be used as the substrate for chromogenic detection.

The preferred immunoassay format for practicing this invention is a forward sandwich assay in which the capture reagent has been immobilized, using conventional techniques, on the surface of the support.

Suitable supports used in assays include synthetic polymer supports, such as polypropylene, polystyrene, substituted polystyrene, e.g., aminated or carboxylated polystyrene; polyacrylamides; polyamides; polyvinylchloride, etc.; glass beads; agarose; nitrocellulose, etc.

Immunoblots are run using conventional techniques. The ras p21 proteins do not have to be immunoconcentrated prior transferring to the nitrocellulose filters.

The examples discussed below are intended to illustrate the invention and should not be construed as limitations.

The following cell lines were used in examples discussed below:
1. PSV-13—This is an NIH3T3 cell that was transformed by overexpression of the normal Harvey-Ras p21.
2. NIH3T3—This is a non-transformed, but immortalized, mouse fibroblast cell.
3. NIH3T3 (SW480)—This is an NIH3T3 cell that was transfected and transformed with DNA from the human colon carcinoma cell line SW480. SW480 cells contain an activated Ki-ras gene which encodes an activated ras p21 having valine at position 12. Thus, the NIH3T3 (SW480) expresses this activated cellular human p21 with valine at position 12.
4. PSV-LM-EJ or LMEJ—This is an NIH3T3 cell transfected and, thus, transformed with an activated cellular Ha-ras p21 with valine at position 12. The DNA transfected into NIH3T3 cells was derived from the human bladder carcinoma, designated EJ. Thus, the PSV-LMEJ contains an activated p21 with valine at position 12.
5. S-2—This is an NIH3T3 cell transfected with and, thus, transformed with an activated Ha-ras p21 encoding glutamic acid at position 12.
6. 3T3-N-ras or NIH3T3 (N ras)—This is a cell line transfected and transformed with an activated N-ras gene.
7. KNRK—This is a cell line consisting of a normal rat kidney cell transformed by the viral-Kirsten gene which encodes an activated p21 with serine at position 12. v-Ha-ras—This is an NIH3T3 cell transformed by the viral-Harvey ras gene which encodes an activated p21 with arginine at position 12.
9. NIH-Zip Ras K-3—This is an NIH3T3 cell transformed by overexpression of the normal Ki-ras p21 encoding glycine at position 12.
10. AML-1—This is an NIH3T3 cell transfected with DNA from a human acute myelogenous leukemia cell line which contains an activated N ras p21 containing aspartic acid at position 13.
11. T144-1—This is an NIH3T3 cell transfected with DNA from a human breast carcinosarcoma cell line (HSO578t) which contains an activated p21 containing aspartic acid at position 12.
12. A2182—This is a human carcinoma cell line which contains an activated p21 with arginine at position 12.
13. NIH3T3(cys-13)—This is an NIH3T3 cell line transfected and, thus, transformed with an activated H ras gene encoding an activated p21 with cysteine at position 13.
14. A549—This is a human lung carcinoma cell line reported to express an activated p21 containing serine at position 12.

The following procedure was used to prepare tumors in nude mice: Cells were harvested from tissue culture flasks, centrifuged to form a pellet and diluted to a concentration of 40–80×106 cells/ml. 0.25 ml or 10–20×106 cells were inoculated in the hind quarter of the mouse subcutaneously. Mice were then observed daily for the appearance of tumors. The tumors were removed at 2–4 cm in size. Plasma was prepared by collecting blood into tubes coated with EDTA.

EXAMPLE 1

Detection of Ras p21 in Culture Fluids

Various tumor cell lines known to express either the normal or activated forms of the ras p21 were grown in culture flasks for several days and the culture fluids were removed to determine whether normal or activated forms of ras p21 proteins were present in the fluids.

Two biochemical procedures were utilized to determine whether ras p21 was released into the cell culture fluid. Initially the ras p21s were inmunoconcentrated from the fluids using an anti-p21 pan reactive monoclonal antibody designated ras 10. The ras p21s were then detected using an immunoblot procedure called a western blot.

4 ml of cell culture fluid obtained from cells growing in culture, such as PSV-13 and NIH3T3 (SW480) or cell culture growth medium was incubated for one hour with an anti-p21 monoclonal antibody e.g. Ras 10) as discussed above. After incubation with the anti-p21 monoclonal antibody, a complex of rabbit anti-mouse immunoglobulin protein A sepharose was added to the tube containing the culture fluid and the anti-p21 monoclonal antibody for 30 to 60 minutes to capture the anti-p21 monoclonal antibody. After a one hour incubation period, the material was centrifuged to form a pellet. The pellet was washed several times with RIPA which is a buffer containing 1.0% Triton X-100, 0.1% sodium dodecylsulfate (SDS), 0.15M sodium deoxycholate, 0.15M sodium chloride, 0.05 TRIS-HCl, and 1 mM phenylmethylsulfonylfluoride (PMSF) which is a protease inhibitor. The final wash was completed with a sodium dodecylsulfate reducing buffer containing 2- mercaptoethanol (2-ME). The resulting material was heated for 5 minutes at 100° C. The resulting fluid containing the ras p21 was then applied to a 12.5% polyacrylamide gel. Cellular proteins that had been released into the culture fluid by treatment with the reducing buffer and heating were separated according to molecular weight by running an electric current through the gel. Proteins were then electrophoretically transferred to nitrocellulose membranes which were blocked with phosphate buffered saline (PBS) Containing 5% bovine serum albumin (BSA). The ras protein impregnated nitrocellulose was incubated for one hour with anti-p21 pan reactive monoclonal antibody designated Ras 10 described above, a monoclonal antibody designated DWP which is described above or a negative control antibody. Unless otherwise indicated, normal mouse serum was used as the negative control.

After incubation with Ras 10, DWP or a negative control antibody, the nitrocellulose membranes were washed three times with PBS-NP-40 solution. These membranes were then incubated for one hour with an anti-mouse immunoglobulin coupled to horseradish peroxidase (HRP) to detect the mouse antibodies. The anti-mouse immunoglobulin-HRP conjugate was purchased from Bio-Rad Laboratories (Richmond, Calif.).

Membranes were then washed three times with PBS-NP-40 solution and incubated with 4-chloro-1-naphthol as substrate to complete the reaction.

Results demonstrated, surprisingly and unexpectedly, that ras p21 proteins from a variety of cell lines could be detected in the culture fluid using the methodology employed herein, namely, immunoconcentrating ras p21 with an anti-p21 monoclonal which was generated against recombinant Ha-ras p21 having an arginine substitution at position 12 (Ras 10) and, then, detecting in a western blot format using monoclonal antibodies such as those described above. Results also demonstrated that activated p21s containing a valine substitution at position 12 could be detected in culture fluid of NIH3T3 (SW480) using the monoclonal antibody designated DWP which is described above.

A similar experiment was conducted using culture fluids obtained from the PSV-13. Using the methodology described above, p21 was detected by using anti-p21 pan reactive monoclonal antibody Ras 10 as the immunoconcentrating reagent and as the blotting reagent. When DWP was used as a blotting reagent, it did not blot p21 from the PSV-13 cell line because PSV-13 does not express an activated ras p21 protein containing the amino acid valine at position 12.

Other experiments were performed with culture fluids from cell lines identified as PSV-LM-EJ and NIH-3T3 (SW480) which were described above. Ras 10 was used to immunoconcentrate the p21 proteins. Ras 10, DWP and a negative control were used in the blotting step. Ras 10 and DWP reacted with ras p21 proteins from the PSV-LM(EJ) and NIH 3T3 (SW480) derived culture fluid. In contrast, the negative control did not react with culture fluids containing mutated p21 proteins. Thus, activated p21 was detected in cell culture fluids derived from cell lines known to express an activated ras p21 protein containing valine at position 12.

EXAMPLE 2

Detection of Activated and Normal p21s in Mice Serum Using an Immunoblot

Approximately 10–20×106 PSV-LM-EJ cells or 10–20×106 PSV-13 cells described above were inoculated subcutaneously into separate nude mice to produce tumors. Once these mice developed tumors, they were sacrificed and blood was taken from them. The blood was then evaluated for the presence of p21 shed into the blood by the growing tumor cells. The evaluation was made by using the immunoconcentrating and western blotting techniques described above and the immunoassay format described below in Example 3.

Blood from mice bearing PSV-LM-EJ tumors was found to react with DWP in a western blot which demonstrated the presence of mutated p21 protein containing the amino acid valine at position 12 in the blood of these tumor bearing mice. Blood from mice injected with PSV-13 did not react with DWP but did react with anti-p21 pan reactive antibody, Ras 10, which demonstrated the presence of normal ras p21 protein in murine blood.

These surprising and unexpected results indicated that the detection of activated p21 in the blood of mice injected with PSV-LM-EJ cells demonstrated that activated ras p21 can be detected in the blood of tumor bearing mice. Furthermore, these results demonstrated that normal ras p21 protein was present in the blood of mice bearing PSV-13 tumors which express normal ras p21 protein.

EXAMPLE 3

Immunoassay Protocol

This describes the general immunoassay protocol.

Microtiter plate wells are coated initially with at least one of the antibodies described above or with cocktail of antibodies.

Amounts of antibody can range from about 2,000 ng to about 500 ng in carbonate buffer (pH 9.6) are transferred to a microtiter plate well and incubated overnight at 4° C. After the antibody or antibodies are immobilized on the surface of the microtiter plate well, excess fluid is decanted and 200 μl of blocking buffer is added to each well. The blocking buffer contained 10% lactose and 2% bovine serum albumin. Blocking buffer prevents nonspecific binding. Excess blocking buffer is decanted. Another 200 μl of the blocking buffer is added to the microtiter plate wells and incubated for one hour. Buffer is decanted and the plate is air dried.

Sample (cell lysate, tumor lysate or various fluids) is added to the wells and allowed to incubate at room temperature for a specified period of time which can range from a few hours to overnight. The wells are washed six times with phosphate buffered saline (PBS) and 0.05% Tween 20. Plates are washed three times, rotated 180° and washed three more times.

The detector reagent is a detectably labeled antibody or cocktail of antibodies and is added to the wells in 50% rabbit serum and incubated for thirty minutes. Preferably, the detector antibody or antibodies are coupled to biotin.

After plates are washed six times with PBS and 0.05% Tween, streptavidin-horseradish peroxidase is added in 1% bovine serum albumin to each well and incubated for thirty minutes at 37° C. Plates are washed another six times prior to adding orthophenylenediamine (OPD) in citrate buffer (pH 5.0) for thirty minutes at 37° C. to effect detection. 4.5M sulfuric acid is added to terminate the reaction.

FIG. 1 is a diagram illustrating the basic sandwich immunoassay format.

EXAMPLE 4

Detection and Quantitation of Ras p21s From Cell and Tissue Extracts

Microtiter plate wells were coated with an anti-p21 monoclonal designated ras 11 as described above or with monoclonal antibodies specific for Ha or N ras p21 proteins.

Lysates used in these experiments came from the following cell lines which were described above: PSV-13, NIH3T3, NIH3T3 (SW480), KNRK, and NIH-(N-ras).

Cell lysates or lysates obtained from tissue extracts of nude mouse tumors can be obtained using techniques available to those of ordinary skill in the art. Lysates from cells grown in culture or from tumors originating in mice inoculated with cells from culture were then added to the plates coated with an anti-p21 pan reactive rabbit polyclonal antibody and allowed to incubate overnight. After incubation, plates were washed to remove any unreacted cell lysate.

p21 present in the cell lysate bound to the antibodies coated onto the plates could be detected using a biotinylated anti-p21 ras 10 monoclonal as discussed above. The biotinylated monoclonal antibody was then chromogenically detected using streptavidin horseradish peroxidase and o-phenylenediamine as the substrate.

The results demonstrated that the plates coated with anti-H monoclonal antibodies were able to detect only the H ras p21 protein and not the Ki2A, Ki2B, or N ras p21 proteins. Plates coated with anti-N monoclonal antibodies were able to detect only the N-ras protein and not the Ha, Ki2A or Ki2B ras p21 proteins. Plates coated with anti-p21 monoclonal designated ras 11 detected p21 proteins from all the cell lines discussed above. Thus, these results show that the H ras and N ras p21s can be detected using the immunoassay format of the invention.

EXAMPLE 5

Rabbit polyclonal anti-p21 pan reactive antibodies were immobilized as the capture reagent on the surface of a microtiter plate. Culture supernatant fluid from two mouse cell lines designated NIH3T3 (SW480) and NIH3T3 cell was reacted with the immobilized capture reagent following the protocol described in Example 3 above. After incubation, plates received anti-p21 Ras 10 labeled with biotin and the immunoassay was performed as described above in Example 3.

Figure 2:
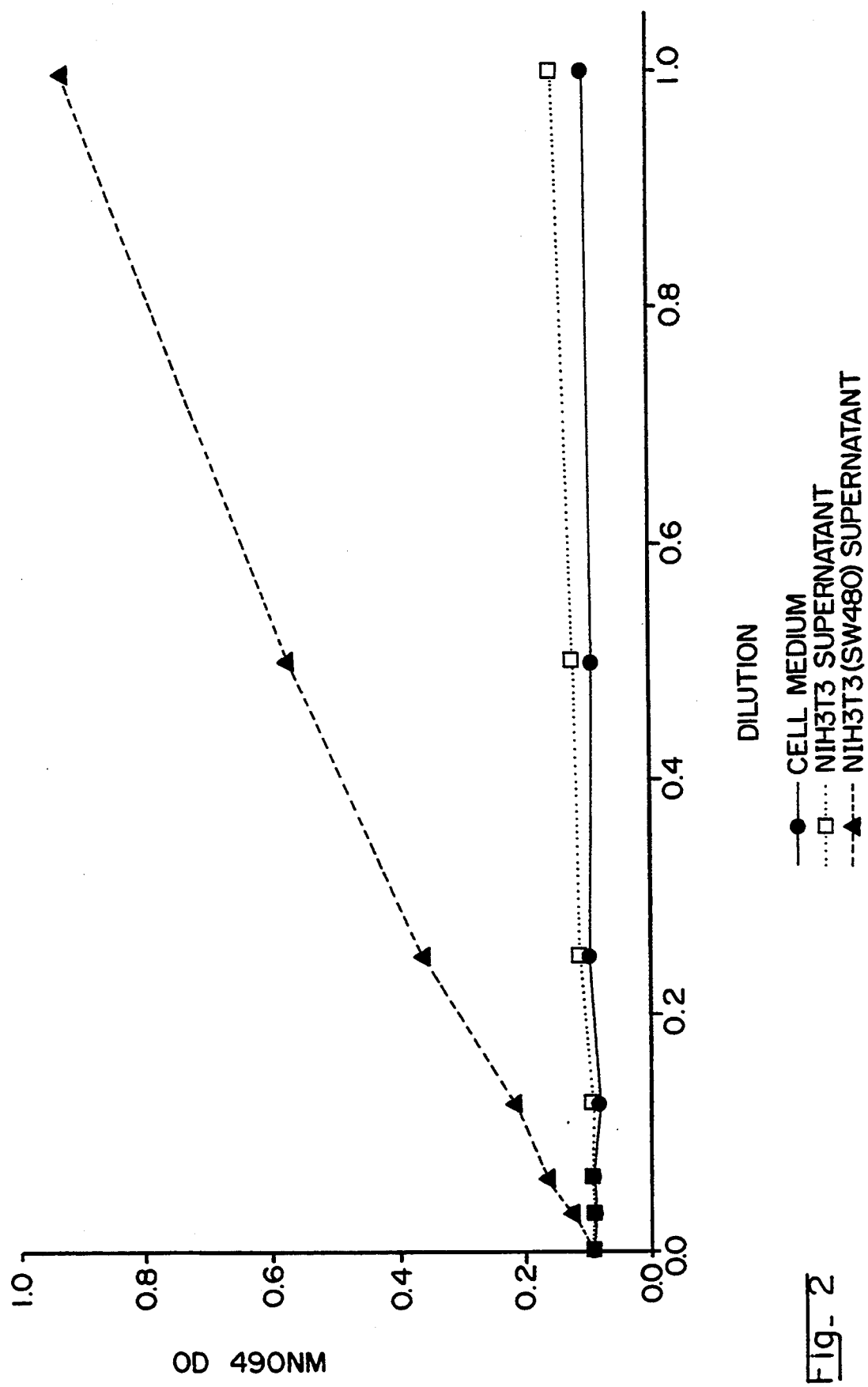
FIG. 2 is a graph showing the detection of ras p21 protein released/shed into culture fluids obtained from cell lines NIH3T3 and NIH3T3 (SW480) using the immunoassay of the invention.

Results are presented in the graph in FIG. 2. The y-axis represents the optical density recordings and the x-axis represents one over the dilution of supernatant fluid.

Results in FIG. 2 demonstrated that ras p21 protein was present in much higher levels in supernatants from NIH3T3 (SW480) cells than in supernatants from NIH 3T3 cells. In fact, very little ras p21 was detected in the NIH 3T3 supernatants. The differences in levels of ras p21 expression was most likely due to major differences in cell growth rate. NIH3T3 (SW480) are transformed NIH3T3 cells where NIH3T3 cell are not transformed.

These results demonstrated that ras p21 protein was released or shed into the culture fluid and the released/shed p21 was detected using the immunoassay format described herein. The immunoassay results agreed with the results of the biochemical analyses discussed in Example 1.

EXAMPLE 6

Detection of Ras p21 Proteins in Plasma of Nude Mice Bearing Subcutaneous Tumors According to the immunoassay and biochemical results discussed above, PSV-13 tumor cells contained higher levels of p21 than PSV LM(EJ) cells. Thus, plasma from mice bearing PSV-13 tumors was believed to contain higher amounts of ras p21 protein than plasma from mice bearing PSV LM(EJ) tumors.

Plasma from three types of mice was evaluated using the immunoassay format described in Example 3. Normal nude mouse plasma, plasma from nude mice bearing the PSV LM(EJ) tumor, and plasma from nude mice bearing the PSV-13 tumor were used in this study.

Affinity purified rabbit anti-p21 pan reactive polyclonal antibody was used as the capture reagent and biotinylated Ras 10 was used as the detector reagent.

Figure 3:
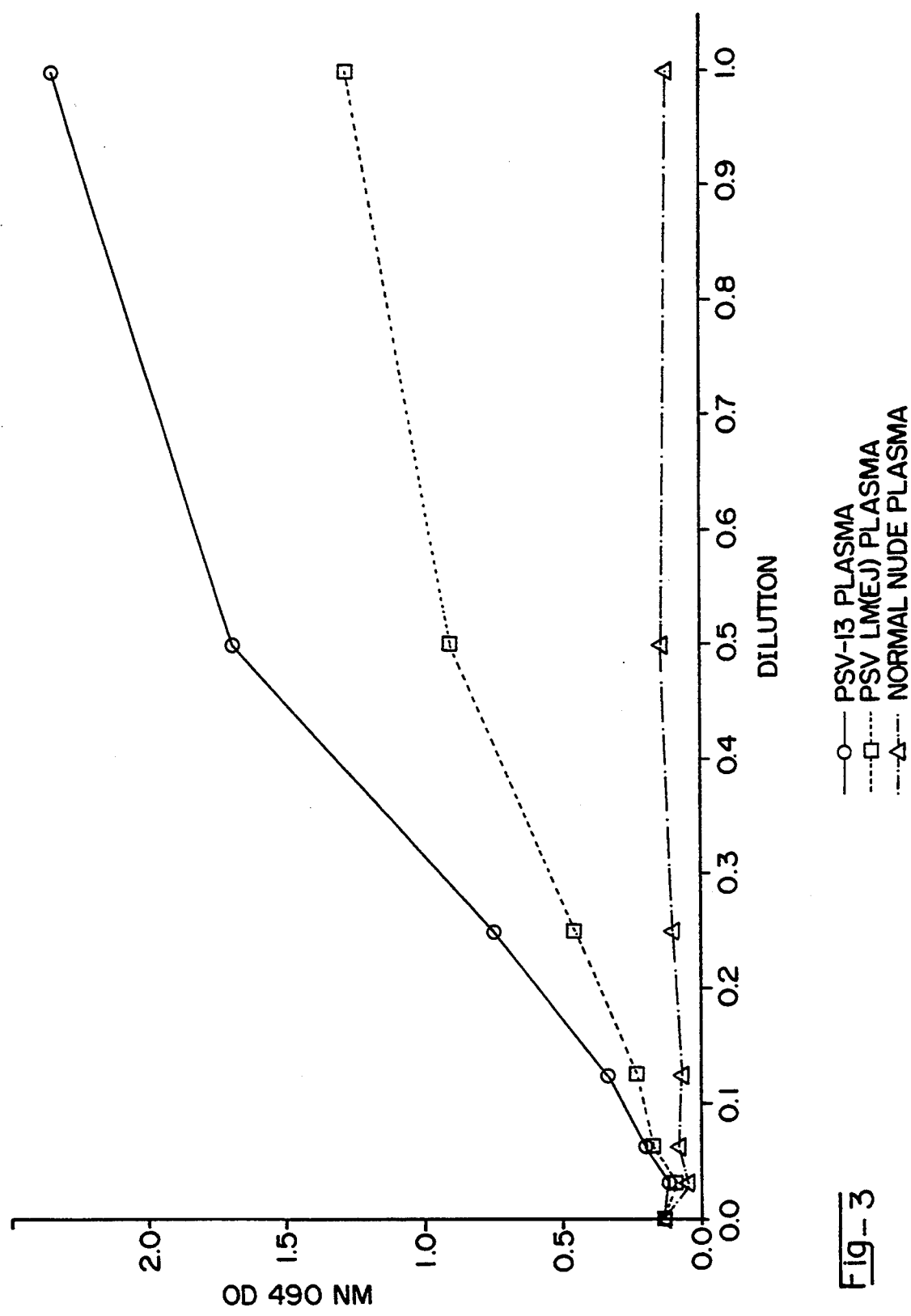
FIG. 3 is a graph showing the detection of ras p21 protein in the plasma of tumor-bearing nude mice using the immunoassay of the invention.

Results are presented in FIG. 3. Low levels of p21 were detected in plasma taken from normal mice indicating that normal ras p21 is present normally in mouse plasma.

Higher levels of p21 were detected in plasma from mice bearing PSV-13 tumors and PSV LM(EJ) tumors. In both cases the p21 levels exceeded the p21 levels detected in plasma obtained from normal mice. These immunoassay results are consistent with the results obtained from the biochemical analyses discussed in Example 2 in that both normal and activated ras p21 proteins were detected using the immunoassay of this invention.

These results were surprising and unexpected because they illustrated not only that ras p21 protein can be shed/released into the circulatory system of mice, but the shed/released p21 proteins were detected in the plasma of mice using the immunoassay of this invention.

Another immunoassay was run using the same capture and detector reagents mentioned above to measure the relative amounts of ras p21 protein in the plasma of PSV LM(EJ) and NIH3T3 (SW480) tumor bearing mice.

Figure 4:
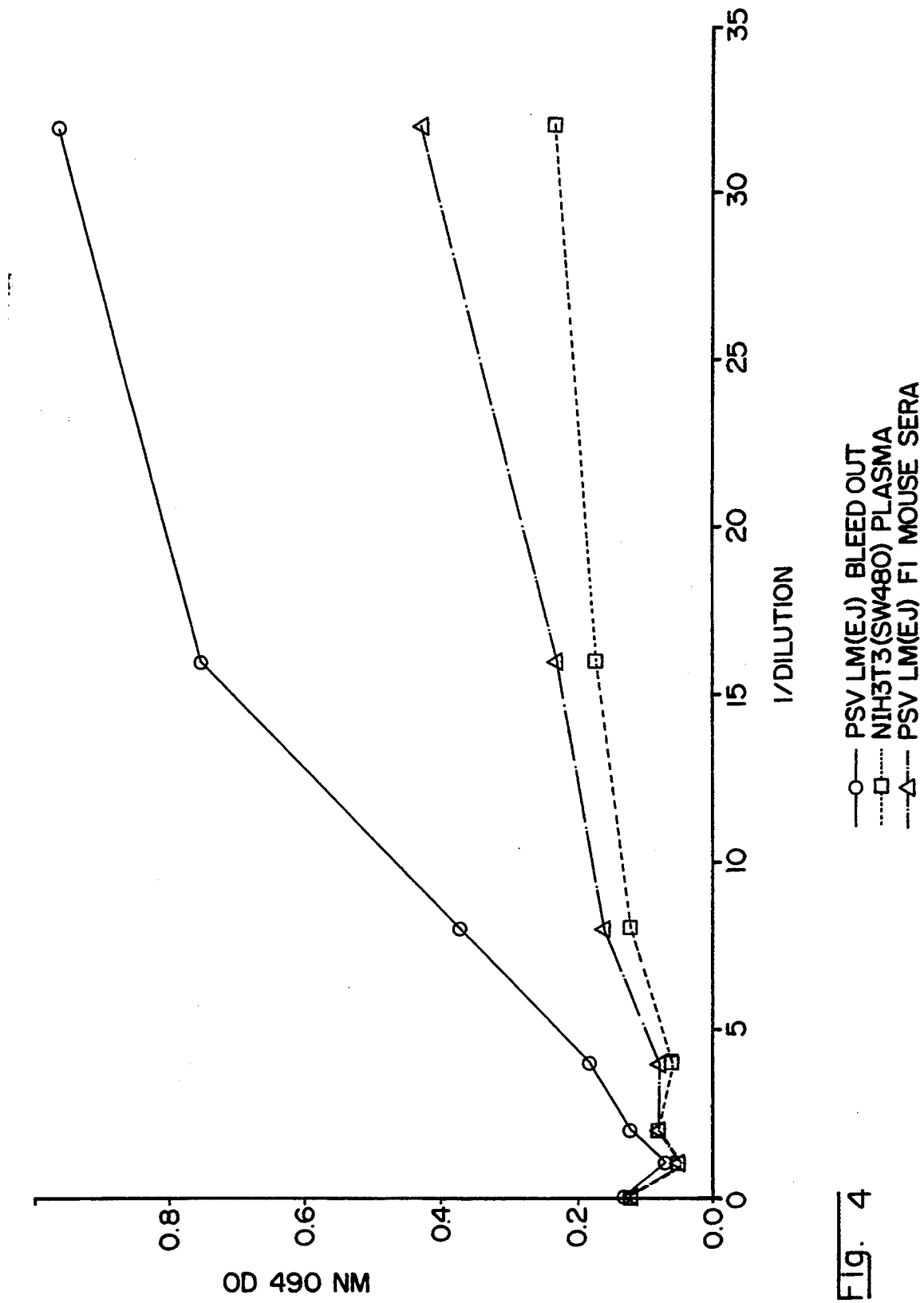
FIG. 4 is a graph showing differential expression of ras p21 proteins in plasma of PSV LM (EJ) and NIH3T3 (SW480) tumor bearing mice using the immunoassay of the invention.

FIG. 4 presents the results obtained from this immunoassay. It shows that plasma from the PSV LM(EJ) tumor bearing mice had higher levels of ras p21 protein than plasma from NIH3T3 (SW480) tumor bearing mice. These results were in agreement with the biochemical results presented in Example 2 above. FIG. 4 also shows that ras p21 in sera of F1 mice was detected using the immunoassay of this invention.

EXAMPLE 7

Evaluation of Human Serum and Plasma for the Presence of Ras p21 Protein

Four human serum specimens (A, B, C, and D) and four human plasma specimens (A, B, C, and D) were obtained from the same four individuals all of whom were normal. These samples were reacted with rabbit anti-p21 pan reactive polyclonal antibodies as the capture reagent and biotinylated Ras 10 as the detector reagent.

Figure 5:
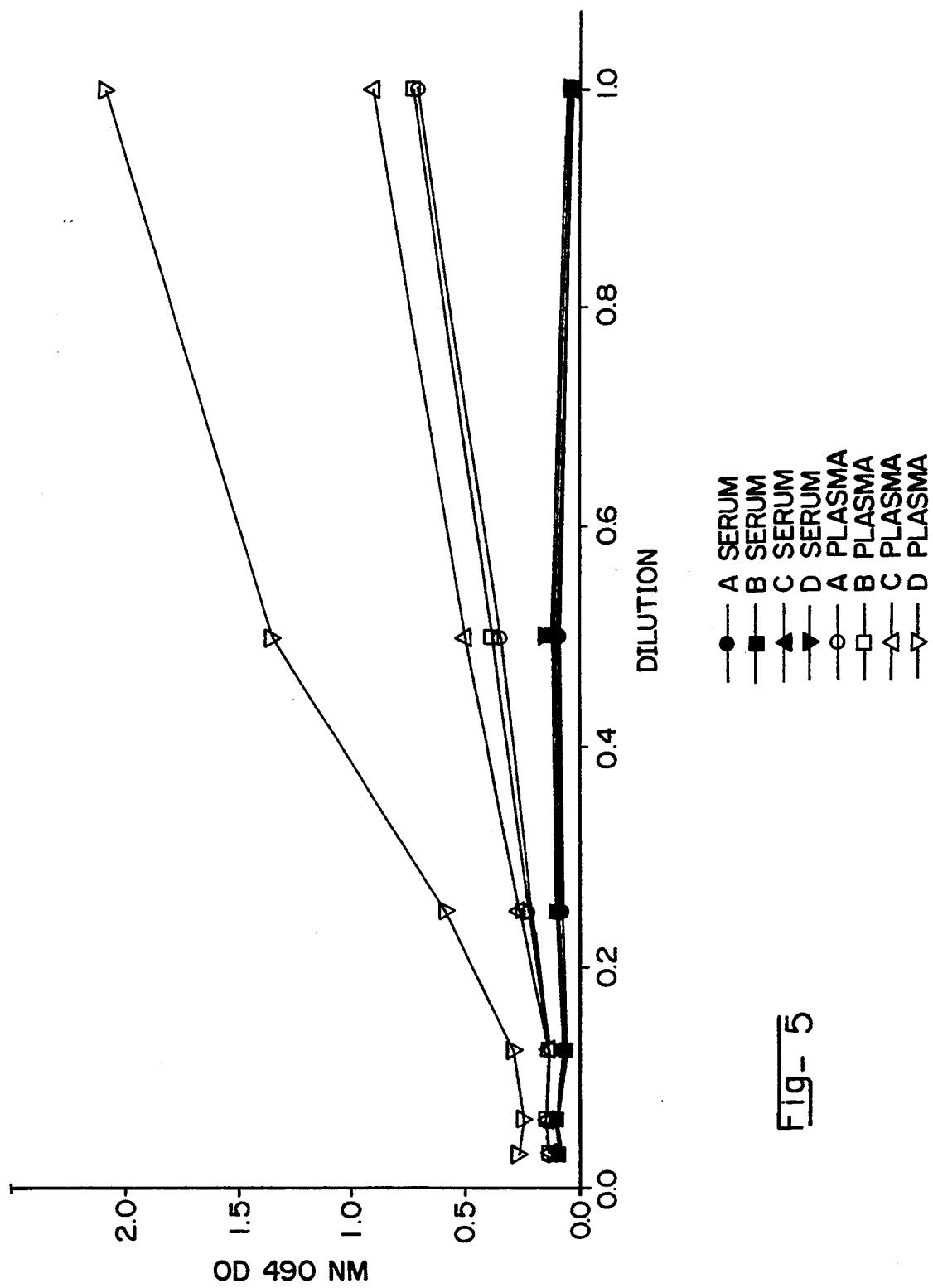
FIG. 5 is a graph showing detection of ras p21 proteins in human plasma using the immunoassay of the invention.
Figure 5A:
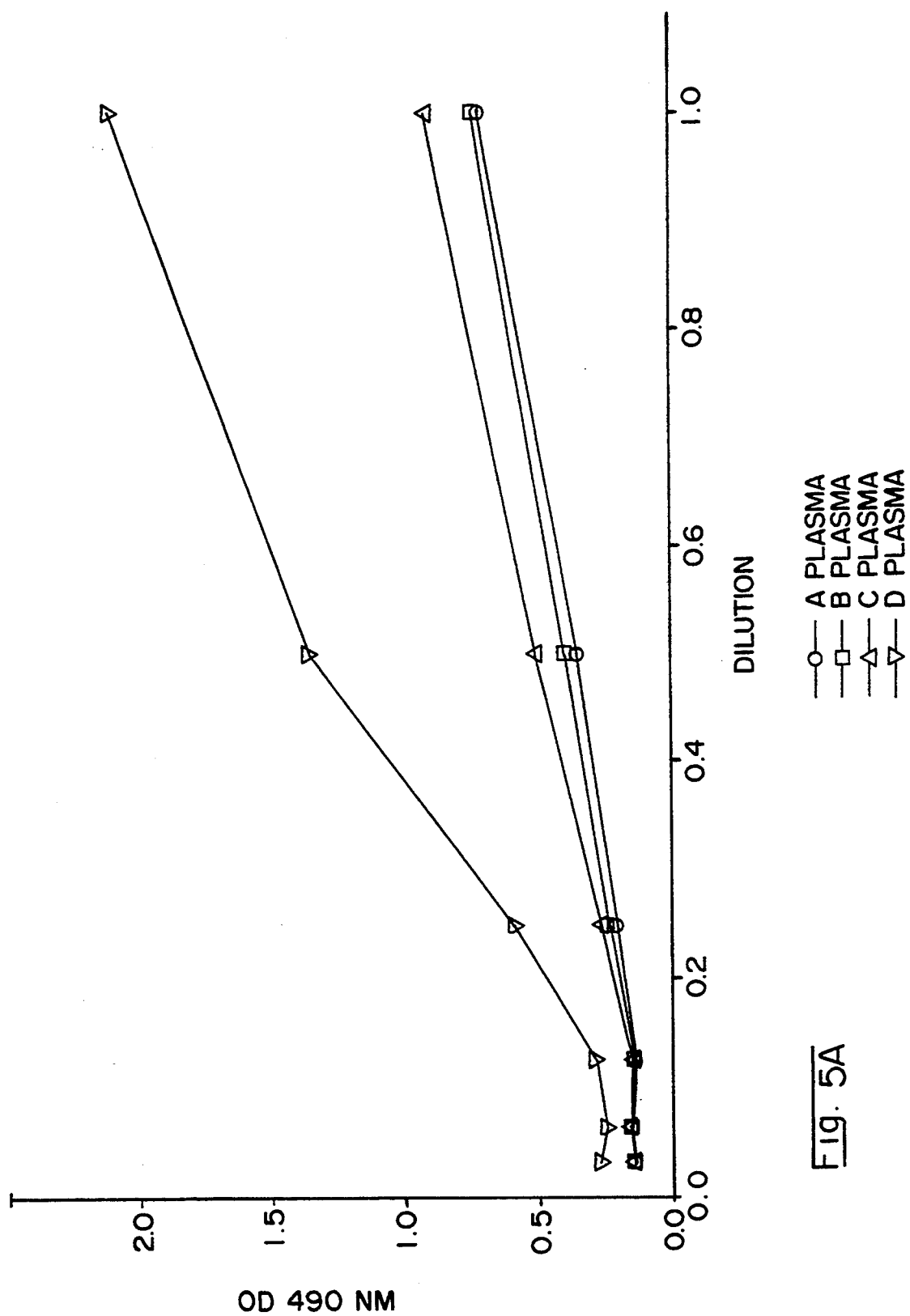
FIG. 5A is a graph showing detection of ras p21 proteins in human plasma using the immunoassay of the invention.

FIG. 5 presents the results for both plasma and serum FIG. 5A presents the results for plasma. Ras p21 protein was not detected in human serum specimens identified as A, B, C, or D. It is not clear whether increased assay sensitivity will aid in the detection of ras in serum. However, various levels of ras p21 protein were detected in the human plasma specimens identified as A, B, C and D.

To confirm the presence of ras p21 protein in the plasma samples and the absence of ras p21 protein in the serum samples, an immunoconcentration and Western blot were run as described below.

Human plasma and serum samples A, B, C, and D were incubated with an anti-p21 pan reactive rabbit polyclonal antibody to immunoconcentrate ras p21 protein from each sample. The procedure was the same as that described in Example 1 except that an anti-p21 pan reactive rabbit polyclonal antibody was used instead of an anti-p21 pan reactive mouse monoclonal antibody.

After immunoconcentration, the immune complex consisting of anti-p21 pan reactive rabbit polyclonal antibody and ras p21 protein was reacted with a complex of goat anti-rabbit immunoglobulin protein A and incubated for one hour. The resulting material was centrifuged to form a pellet which was washed several times with RIPA. A final was was made using sodium dodecylsulfate reducing buffer containing 2-mercaptoethanol (2-ME). The resulting material was heated for five minutes at 100° C. to produce a fluid containing ras p21 protein. The fluid was applied to a 12.5% polyacrylamide gel. Cellular proteins that had been released into the culture fluid by treatment with the reducing buffer and heating were separated according to molecular weight by running an electric current through the gel. Proteins were then electrophoretically transferred to nitrocellulose membranes which had been blocked with PBS containing 5% bovine serum albumin.

The ras p21 impregnated nitrocellulose filter was incubated for one hour with the anti-p21 pan reactive monoclonal antibody and a negative control which was RPC-5 (a myeloma protein).

The nitrocellulose membranes were then washed three times with PBS-NP-40 solution. These membranes were incubated with an anti-mouse immunoglobulin coupled to horseradish peroxidase. Membranes were washed three times with PBS-NP-40 and incubated with 4-chloro-1-naphthol as substrate to complete the reaction.

Biochemical results illustrated that ras p21 protein was immunoconcentrated from the four human plasmas designated A, B, C, and D and visualized by western blot. These biochemical results confirmed that ras p21 protein was detected in human plasma in the immunoassay format described above and no ras p21 protein was detected in the human serum samples.

EXAMPLE 8

Detection and Quantitation of Ras p21 Protein In Three Mouse Cell Lines Containing Human Ras Genes The immunoassay format described in Example 3 was used to determine the presence and level of ras p21 protein in three mouse cell lines containing human ras genes. These cell lines were the following: S-2, PSV LM(EJ), and PSV-13.

As was described before, the capture reagent was an anti-p21 pan reactive rabbit polyclonal antibody and the detector reagent was biotinylated Ras 10.

Western blot studies, discussed in Example 1, above indicated that the S-2 cell line expressed a lower level of ras p21 protein when compared to the ras p21 level expressed by the PSV-13 cell line. The PSV LM(EJ) cell line expressed ras p21 protein at a level which was lower than that expressed by PSV-13 and greater than that expressed by the S-2 cell line.

Figure 6:
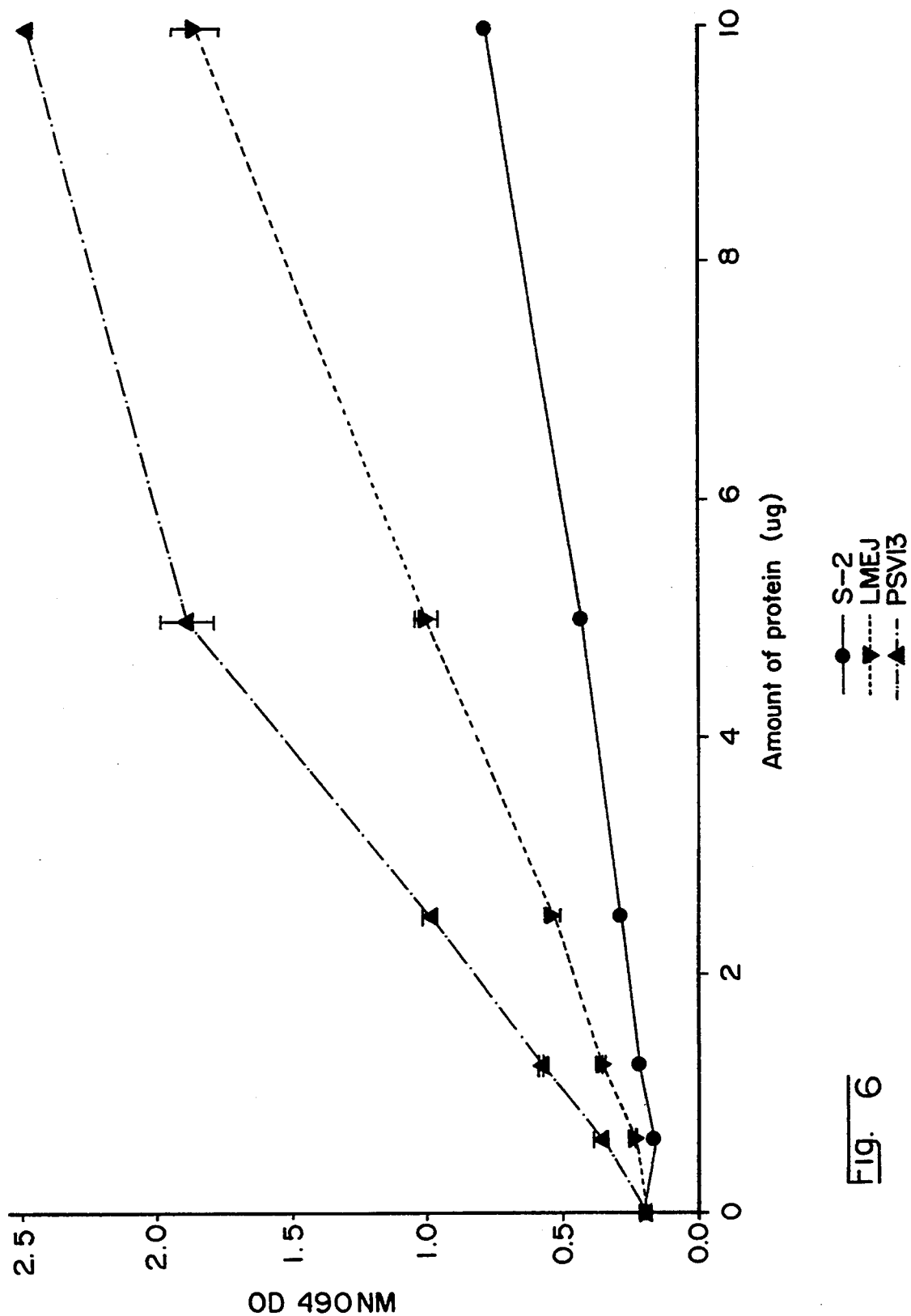
FIG. 6 is a graph showing detection of ras p21 proteins in three mouse cell lines containing human ras genes using the immunoassay of the invention.

FIG. 6 presents immunoassay results which confirm the observations made in the western blot studies.

Figure 7:
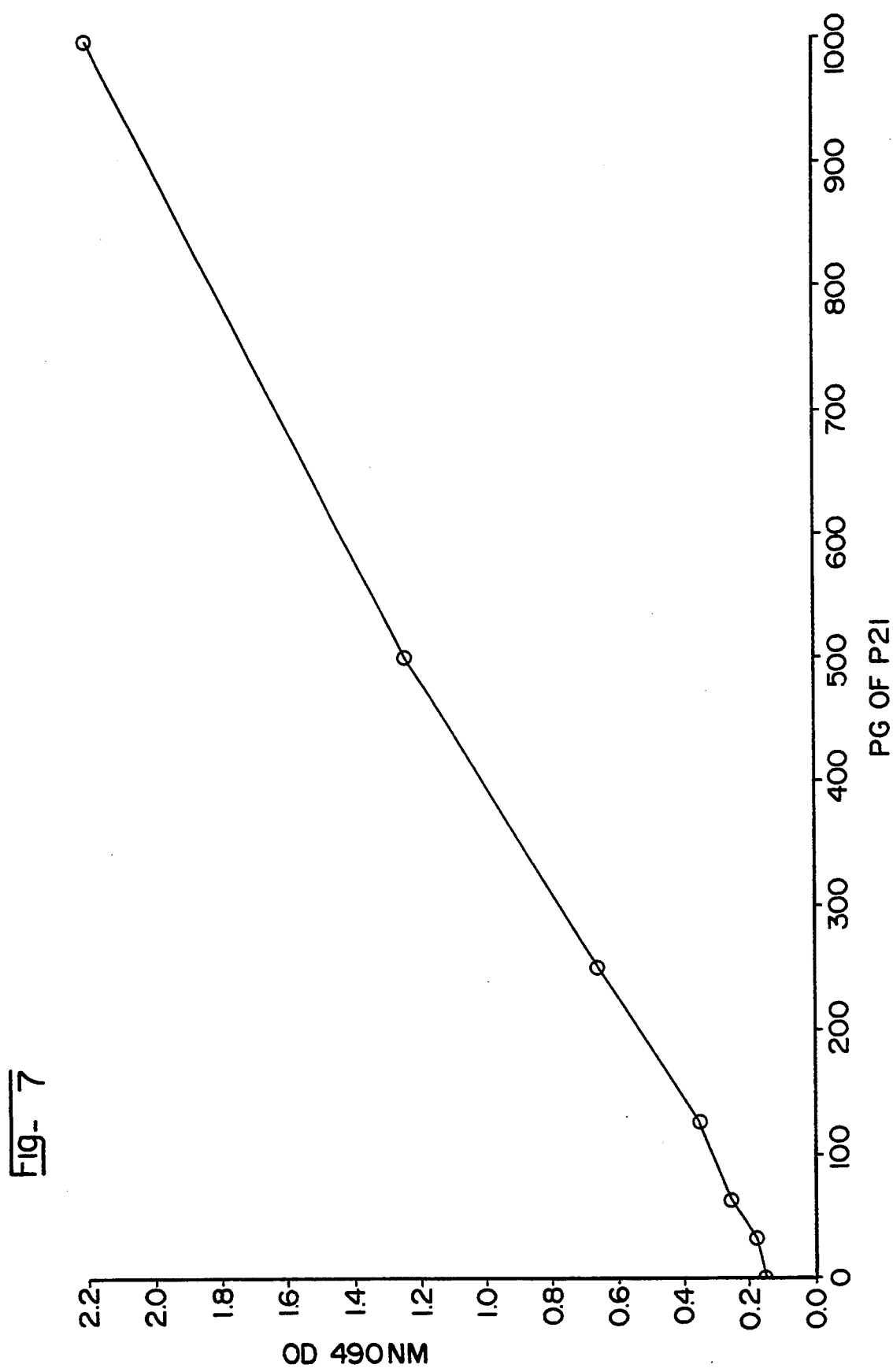
FIG. 7 is a ras p21 standard curve.

Quantitative analyses were made by constructing a standard curve using recombinant Ha ras p21 protein containing arginine at position 12. FIG. 7 presents the standard curve which was constructed by reacting various concentrations of recombinant Ha-ras p21 protein with immobilized anti-p21 pan reactive rabbit polyclonal antibody and detecting captured p21 by using a biotinylated anti-p21 pan reactive mouse monoclonal antibody, Ras 10. The immunoassay format was as described in Example 3 above.

The optical density values obtained were plotted versus the amount of ras p21 protein tested. Results are presented in Table 3 below. Using this standard curve, it was determined that the S-2 cell line contained 24.5 pg of ras p21 protein per μg of cell protein; the PSV LM(EJ) cell line contained 71.3 pg of ras p21 protein per μg of cell protein and the PSV-13 cell line contained 154.0 pg of ras p21 protein per μg of cell protein. These results were consistent with the qualitative observation made using western blot studies.

This demonstrates that the immunoassay format describe in Example 3 can be used to construct a standard curve in order to quantitate the amount of ras p21 present in a sample.

TABLE 3

| | p21 Expression in Tumors | |
|---|---|---|
| Tumors | pg of p21/μg of total proteins | Relative levels of Expression |
| S-2 | 24.5 pg/μg | 1.0 |
| LMEJ | 71.3 pg/μg | 2.9 |
| PSV-13 | 154.0 pg/μg | 6.3 |

EXAMPLE 9

Evaluation of Normal Breast Tissue and Breast Carcinoma

Ten specimens of normal breast tissue and ten specimens of breast carcinoma were obtained from Dr. Daniel Hayes of the Dana-Farber Cancer Institute, Boston, Mass. Dr. Hayes obtained these specimens from ten different patients. These specimens were analyzed using the immunoassay format described in Example 3 above. Anti-p21 pan reactive rabbit polyclonal antibodies were used as the capture reagent and biotinylated Ras 10 was used as the detector reagent.

Figure 8:
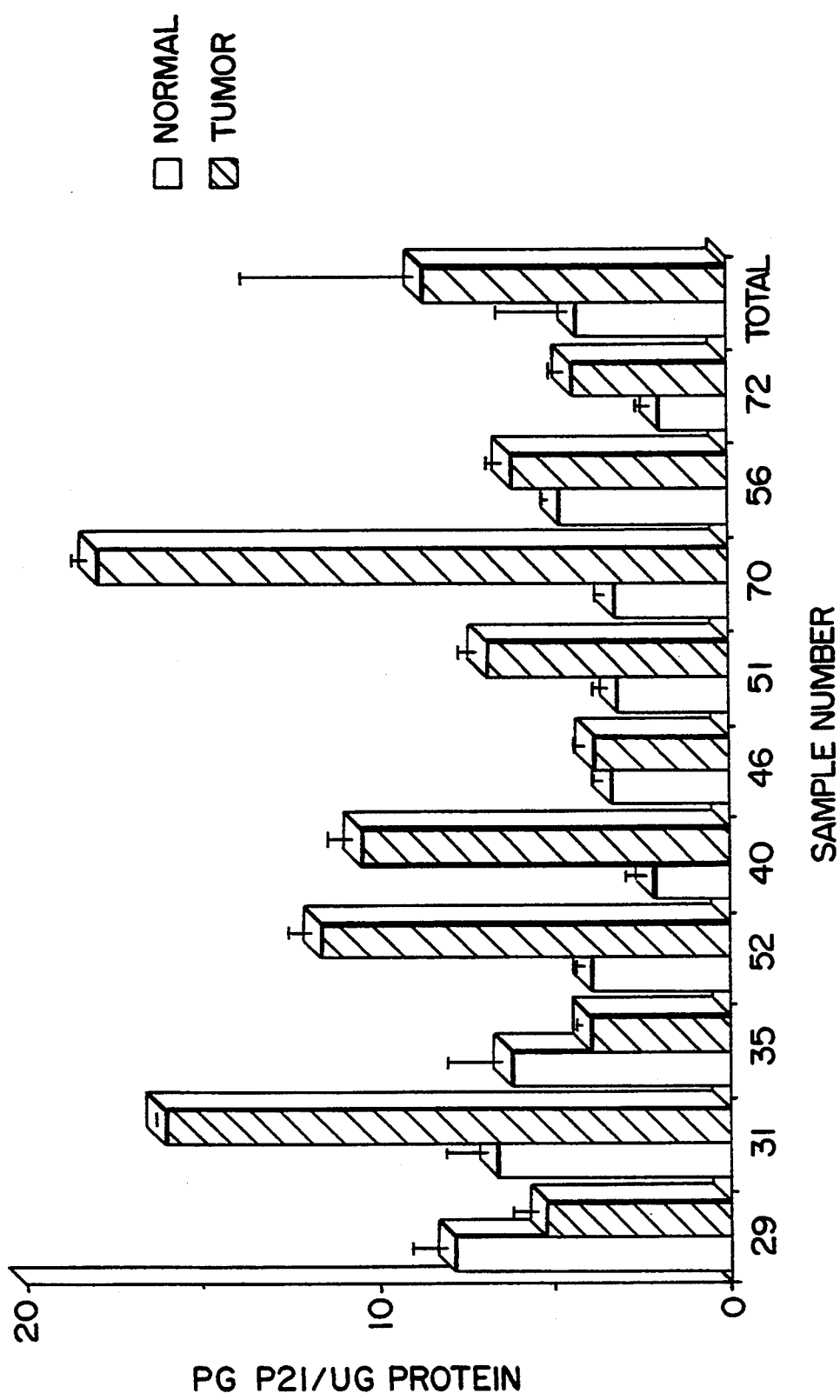
FIG. 8 is a bar graph showing ras p21 protein levels detected in ten specimens of normal human breast tissue and human breast carcinoma using the immunoassay of the invention. Bars represent amount of ras p21 protein expressed as pg of p21 per $\mu$g of protein.

Results are presented in FIG. 8. The bars represent the amount of ras p21 protein expressed as pg of p21 per μg of protein. It was found that normal breast tissue, which is composed primarily of adipose and connective tissue and very little epithelium, contained about 9 pg ras p21/μg of protein whereas at least five of the breast carcinoma specimens, numbers 31, 40, 51, 52 and 70, contained approximately 8 to 18 pg ras p21/μg of protein. Of the ten human breast carcinoma specimens analyzed, about 80% of the specimens showed a higher expression of ras p21 than the normal breast tissue.

EXAMPLE 10

Evaluation of Colon Carcinoma Specimens

Ten samples of human colon carcinoma obtained from Dr. James Radosevich, Northwestern University, Chicago, Ill., were evaluated using the immunoassay format described in Example 3 above. Anti-p21 pan reactive polyclonal antibodies were used as the capture reagent and biotinylated Ras 10 was used as the detector reagent.

Figure 9:
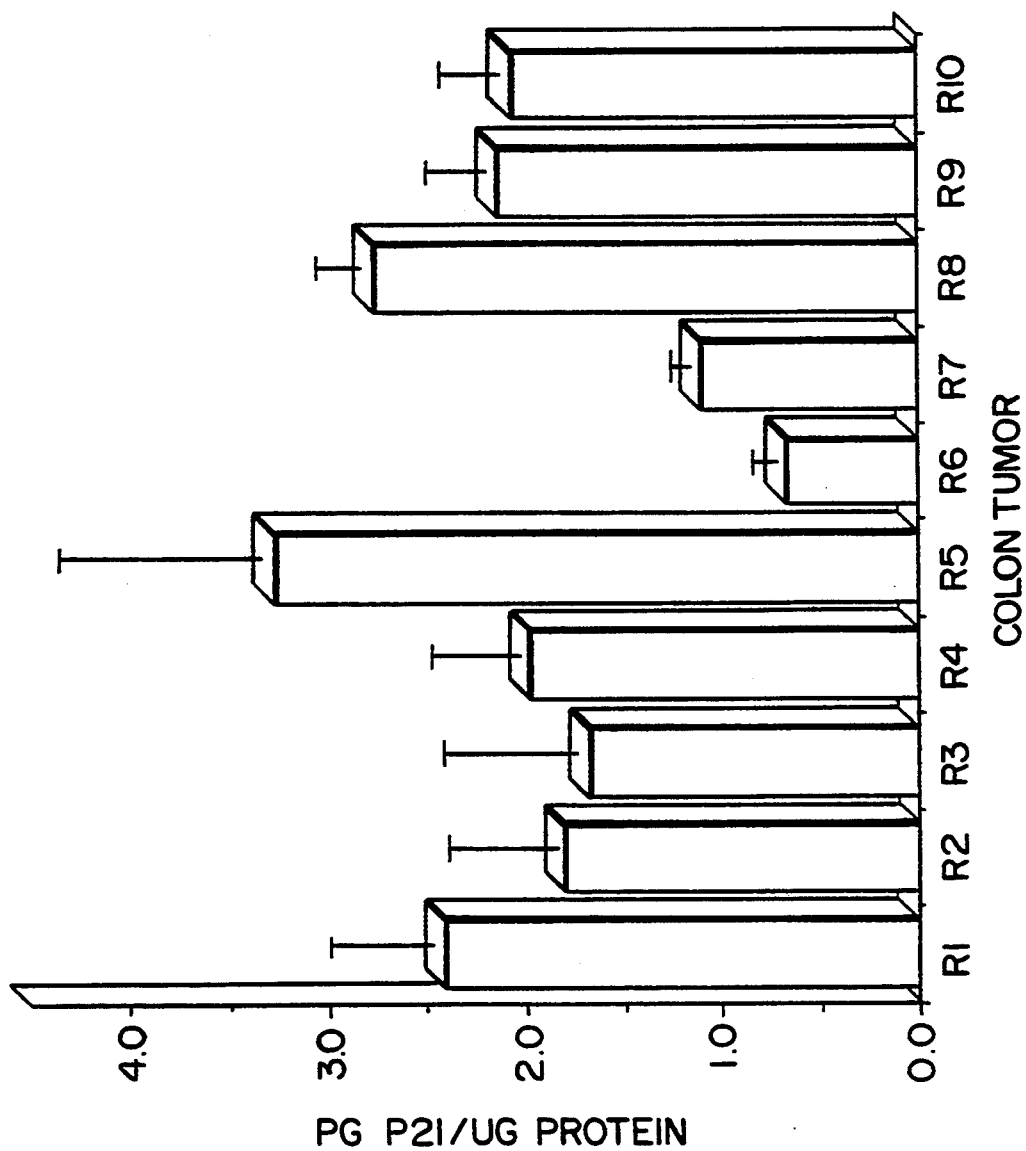
FIG. 9 is a bar graph showing detection and quantitation of ras p21 protein in ten specimens of human colon carcinoma using the immunoassay of the invention. Bars represent amount of ras p21 protein expressed as pg of p21 per $\mu$g of protein.

Results are presented in FIG. 9. It was found that the ras p21 protein level ranged from about 1.0 pg/μg of protein to about 3.5 pg/μg of protein.

The results presented in Example 10 demonstrate that ras p21 protein was detected and quantitated in human human colon carcinoma specimens using the immunoassay format described above.

EXAMPLE 11

The immunoassay format described in Example 3 was used to evaluate the following for the presence of ras p21 protein:
(1) plasma from a normal nude mouse;
(2) plasma from mice bearing PSV LM(EJ) tumors;
(3) plasma from mice bearing PSV-13 tumors;
(4) plasma from mice bearing NIH3T3 (N ras); and
(5) plasma from mice bearing NIH Zip-ras K-3 tumor.

An anti-p21 pan reactive rabbit polyclonal antibody was used as the capture reagent and monoclonal antibody designated DWP was used as the detector antibody. DWP specifically binds to an epitope of activated ras p21 protein containing valine at position 12 and does not bind to an epitope containing glycine at position 12.

Figure 10:
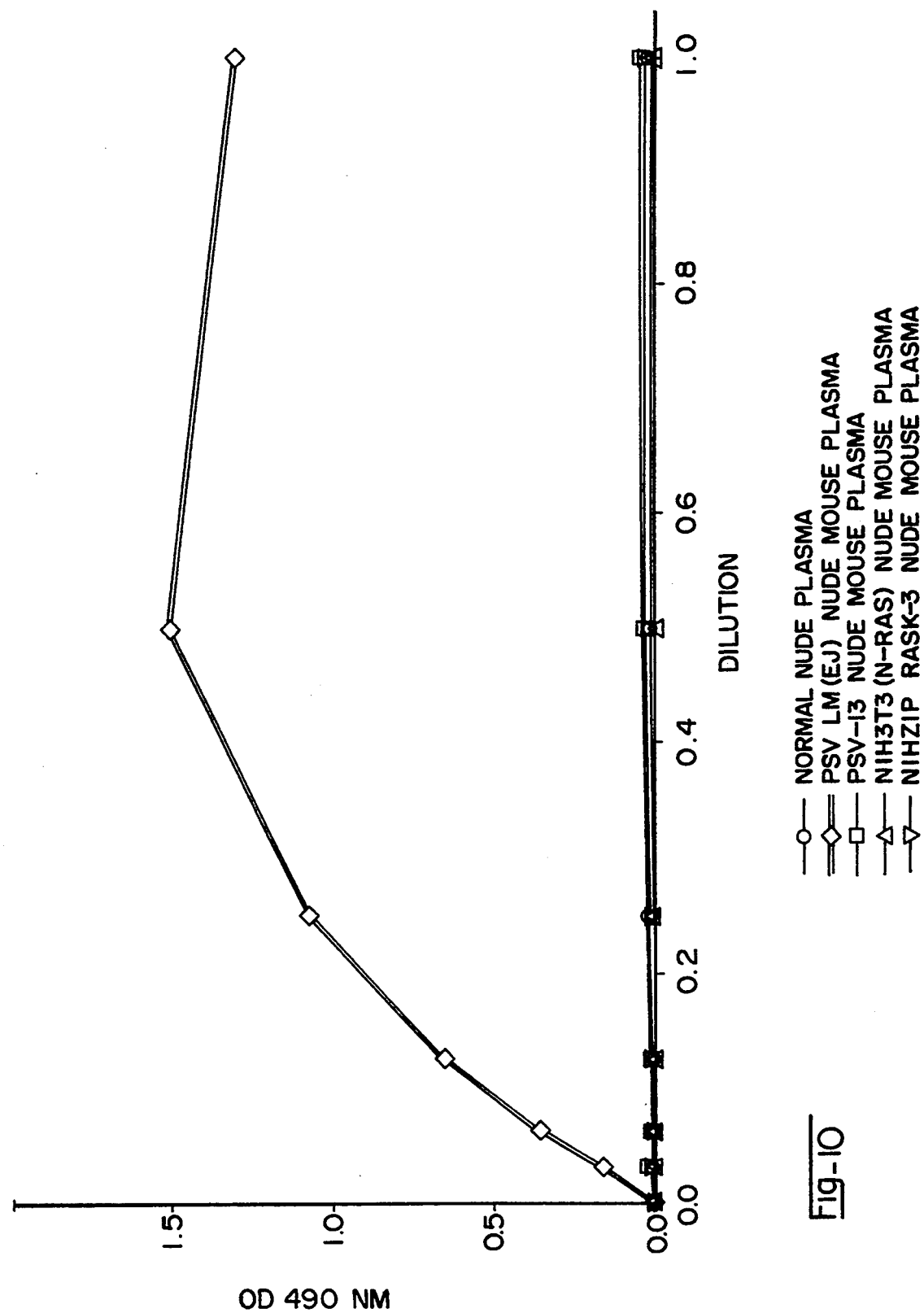
FIG. 10 is a graph showing detection of activated ras p21 protein having valine at position 12 in plasma obtained from tumor-bearing nude mice using the immunoassay of this invention.

Results presented in FIG. 10 show that biotinylated DWP reacted only with plasma obtained from the PSV LM(EJ) tumor bearing mice. This demonstrated conclusively that activated ras p21 protein containing valine at position 12 was released/shed into the plasma of PSV LM(EJ) tumor bearing mice and the released/shed activated ras p21 protein containing valine at position 12 could be detected using this immunoassay format. It is also was in agreement with the results which had been obtained by Western blot.

EXAMPLE 12

Microtiter wells were coated with an anti-p21 pan reactive rabbit polyclonal antibody The immobilized capture reagent was then reacted with a recombinant p21 protein containing glycine, arginine, or aspartic acid at position 12. The recombinant proteins used in this example were obtained from Dr. Geoffrey Cooper, Dana-Farber Cancer Institute, Boston, Mass.

Figure 11:
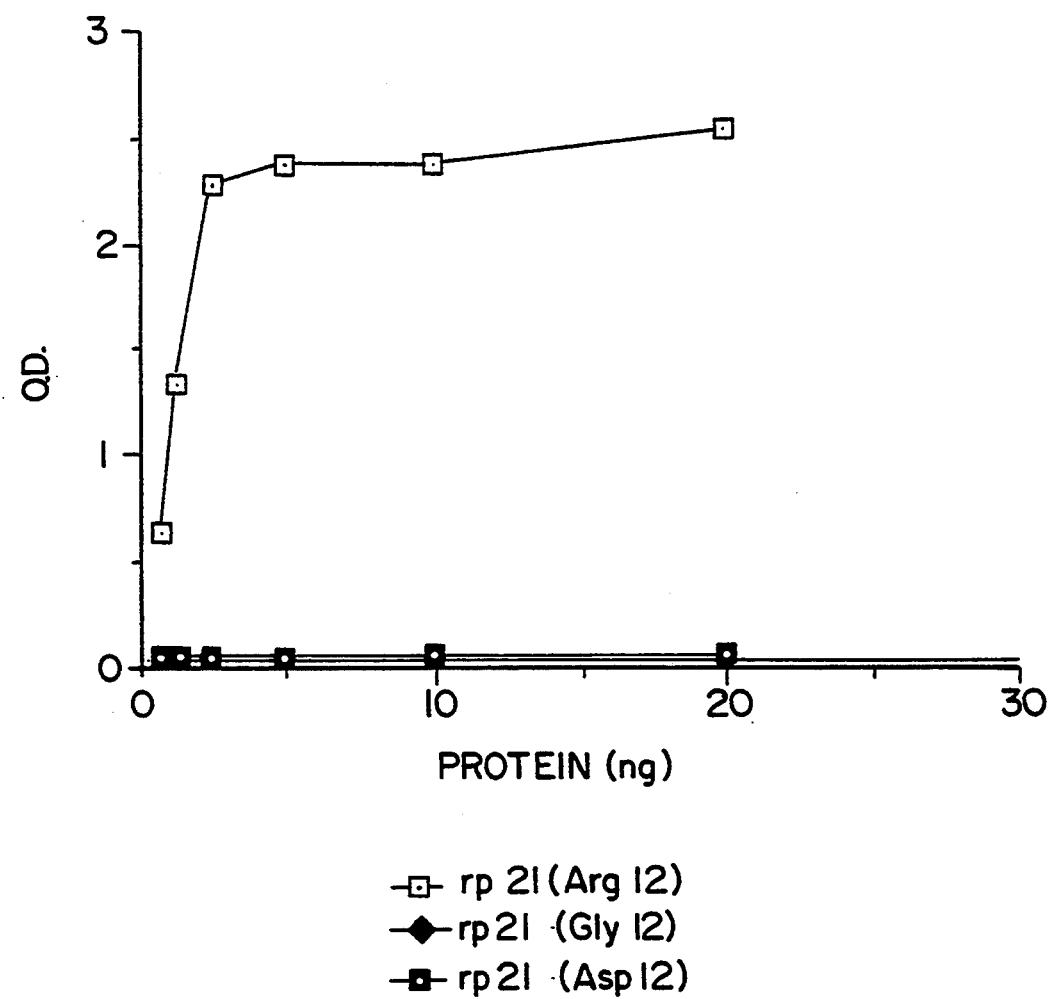
FIG. 11 is a graph showing detection of activated ras p21 protein having arginine at position 12 in recombinant p21 protein having arginine at position 12 using the immunoassay of this invention.

The immobilized anti-p21 pan reactive rabbit polyclonal antibody—ras p21 protein complex was reacted with the detection reagent which was monoclonal antibody, R256 labeled with biotin. R256 is discussed above. The immunoassay results illustrated that biotinylated R256 reacted only with the recombinant ras p21 protein containing arginine at position 12. Thus, it was possible to detect activated ras p21 using the immunoassay format of this invention. FIG. 11 is a graph showing that R256 detected only the recombinant p21 having arginine at position 12.

EXAMPLE 13

A series of experiments was run using eight different cell lines to illustrate the ability of the immunoassay described in Example 3 to detect various activated ras p21 proteins.

The following cell lines were used: (i) cell line AML-1; (ii) cell line T 144-1; (iii) cell line NIH3T3 (cysteine-13); (iv) cell line PSV-13; (v) cell line v-Ha-ras; (vi) cell line A2182; (vii) cell line PSV LM(EJ); and (viii) cell line A549.

An anti-p21 pan reactive antibody was immobilized on microtiter plate wells. After immobilization, the capture reagent was incubated with lysates from one of the eight cell lines described above. The resulting immune complex was assayed for the presence of ras p21 protein by reacting it with one of the different biotinylated antibodies listed below: an anti-p21 pan reactive antibody monoclonal antibody (Ras 10), a monoclonal antibody which specifically binds to an epitope of an activated ras p21 protein having aspartic acid at position 13 and does not bind to an epitope having glycine at position 13 (monoclonal antibody 146), a monoclonal antibody which specifically binds to an epitope of an activated ras p21 protein having aspartic acid at position 12 and does not bind to an epitope having glycine at position 12 (monoclonal antibody 113), a monoclonal antibody which specifically binds to an epitope of an activated ras p21 protein having valine at position 12 and does not bind to an epitope having glycine at position 12 (DWP), a monoclonal antibody which specifically binds to an epitope of an activated ras p21 protein having arginine at position 12 and does not bind to an epitope having glycine at position 12 (R256), and a monoclonal antibody which specifically binds to an epitope of an activated ras p21 protein having serine at position 12 and does not bind to an epitope having glycine at position 12 (S1107-8.3).

Figure 12:
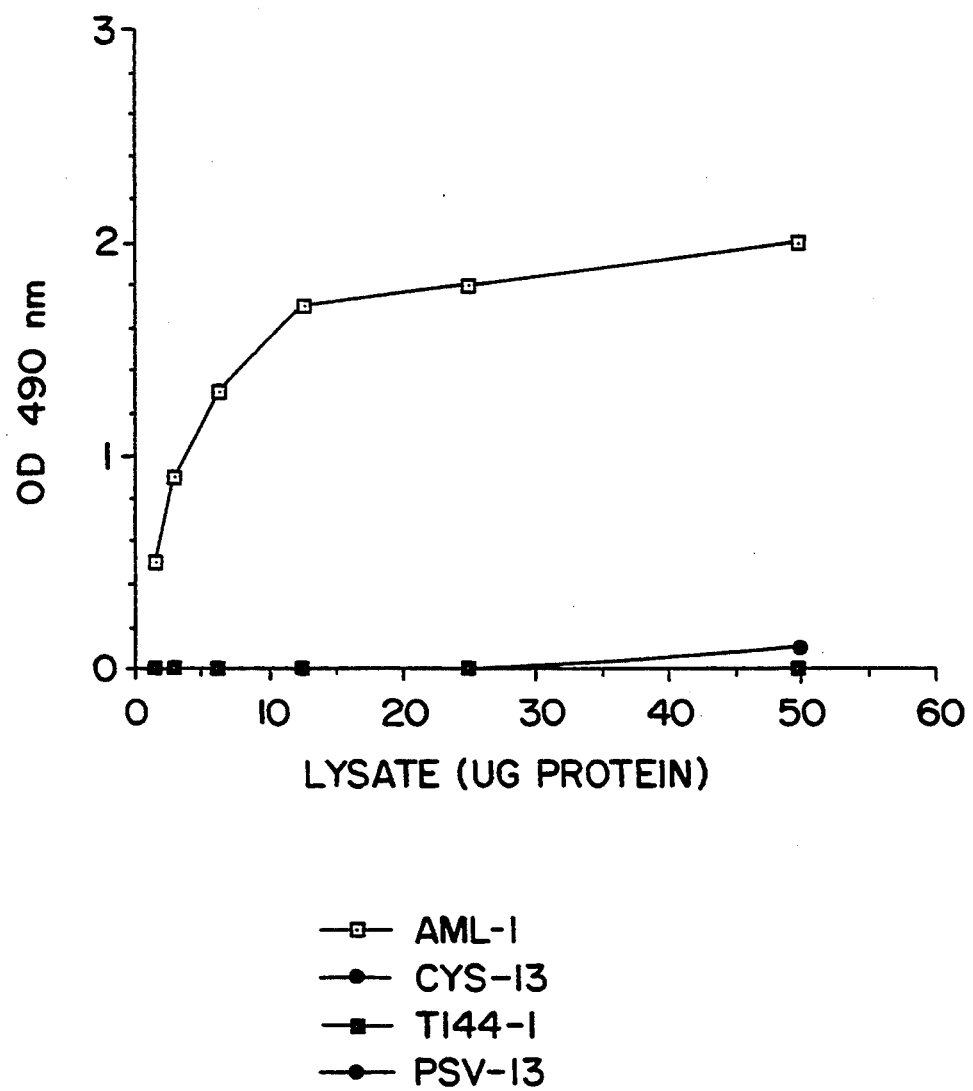
FIG. 12 is a graph showing detection of activated ras p21 protein having aspartic acid at position 13 in cell lysates obtained from cell line AML-1 using the immunoassay of this invention.

Monoclonal antibody 146 specifically detected activated ras p21 protein containing aspartic acid at position 13 expressed by cell line AML-1. FIG. 12 depicts the results obtained using Mab 146 in the immunoassay of this invention.

Monoclonal antibody 113 specifically detected activated ras p21 protein containing aspartic acid at position 12 expressed by cell line T 144-1.

Monoclonal antibody DWP specifically detected ras p21 protein containing valine at position 12 expressed by cell line PSV LM(EJ).

Figure 13:
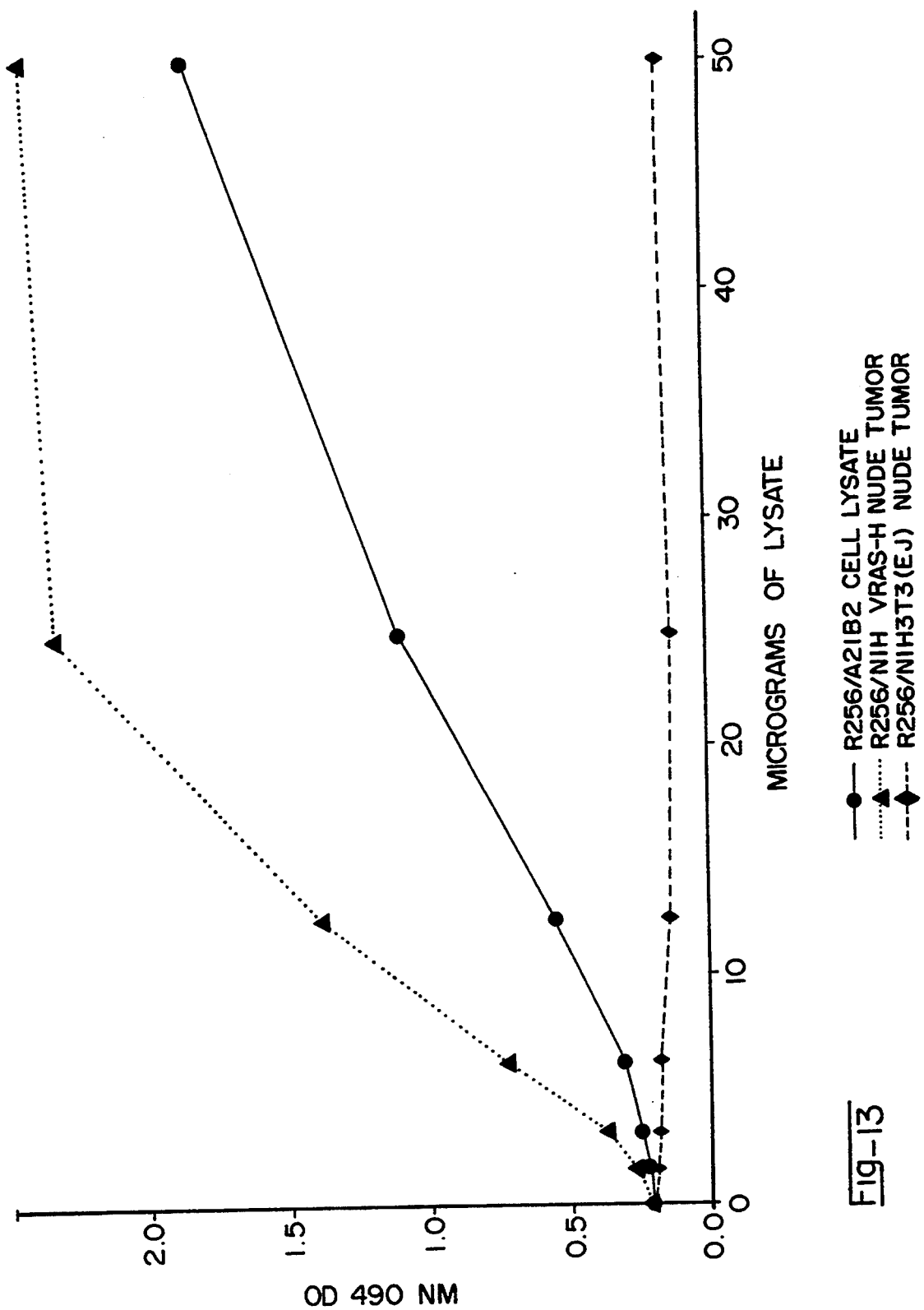
FIG. 13 is a graph showing detection of ras p21 having arginine at position 12 in cell lysates obtained from cell line A2182 and NIH v-H-ras.

Monoclonal antibody R256 specifically detected ras p21 protein containing arginine at position 12 expressed by cell line A2182 and cell line v-Ha-ras. Results are shown in FIG. 13.

Monoclonal antibody S1107-8.3 specifically detected ras p21 containing serine at position 12 expressed by cell line A549.

This conclusively demonstrates the ability of the immunoassay format of the instant invention to detect activated ras p21 proteins.

What is claimed is:

1. An immunoassay for detecting an activated ras p21 in a bodily fluid comprising:
    (a) reacting each of a plurality of samples of the bodily fluid with an immobilized anti-p21 pan reactive antibody as a capture reagent so as to form complexes with any activated ras p21 present in the samples;
    (b) reacting each of the resulting samples of step (a) with (i) a detectably labeled, or (ii) an unlabeled, monoclonal antibody selected from the group consisting of (i) monoclonal antibodies which specifically bind to an epitope of an activated ras protein having an amino acid substitution of arginine, glutamic acid, aspartic acid, serine, valine or cysteine at position 12 but do not bind to an epitope containing glycine at position 12, (ii) monoclonal antibodies which specifically bind to an epitope of an activated ras protein having an amino acid substitution of arginine, aspartic acid or valine at position 13, but do not bind to an epitope containing glycine at position 13, and (iii) monoclonal antibodies which specifically bind to an epitope of an activated ras protein having an amino acid substitution of histidine, lysine, leucine or arginine at position 61, but do not bind to an epitope containing glutamine at position 61, the monoclonal antibody capable of binding to an epitope on the activated ras p21 which is both different from any epitope with which the capture reagent reacts and is not present in normal ras p21; and (c) detecting either (i) the unlabeled monoclonal antibody with a labeled antibody specific for the unlabeled monoclonal antibody, or (ii) the labeled monoclonal antibody, within one of the reaction products of step (b) so as to thereby detect the activated ras p21 in the bodily fluid.

2. The immunoassay of claim 1, wherein the monoclonal antibody of step (b) is selected from the group consisting of (i) monoclonal antibody produced by a hybridoma selected from the group consisting of hybridoma DWP (ATCC Accession No. HB 8698), hybridoma E184 (ATCC Accession No. HB 9194), hybridoma E170 (ATCC Accession No. HB 9195), hybridoma R256 (ATCC Accession No. HB 9196), hybridoma D113 (ATCC Accession No. HB 10086), hybridoma D205 (ATCC Accession No. HB 10061), hybridoma D210 (ATCC Accession No. HB 10083), hybridoma S1107-8.3 (ATCC Accession No. HB 10060), hybridoma C-1119-9 (ATCC Accession No. HB 10084) and hybridoma C-1119-10 (ATCC Accession No. HB 10088); (ii) monoclonal antibody produced by a hybridoma selected from the group consisting of hybridoma D753-13(129) (ATCC Accession No. HB 9632), hybridoma D765-13(146) (ATCC Accession No. HB 9633), and hybridoma V647-13 (ATCC Accession No. HB 9634); and (iii) monoclonal antibody produced by a hybridoma selected from the group consisting of hybridoma R61-1 (ATCC Accession No. HB 10063), hybridoma R61-2 (ATCC Accession No. HB 10069), hybridoma R61-3 (ATCC Accession No. HB 10071), hybridoma R61-4 (ATCC Accession No. 10062), hybridoma L61-1 (ATCC Accession No. HB 10068), hybridoma L61-2 (ATCC Accession No. HB 10073), hybridoma H61-1 (ATCC Accession No. HB 10070), hybridoma H61-2 (ATCC Accession No. HB 10092), hybridoma H61-3 (ATCC Accession No. 10089), hybridoma H61-4 (ATCC Accession No. 10087), and hybridoma H61-5 (ATCC Accession No. HB 10090).

3. The immunoassay of claim 1 or 2, wherein the bodily fluid is plasma.

4. An immunoassay for detecting an activated ras p21 in a bodily fluid comprising:

(a) reacting each of a plurality of samples of the bodily fluid with an immobilized anti-p21 pan reactive antibody as a capture reagent so as to form complexes with any activated ras p21 present in the samples;

(b) reacting each of the resulting samples of step (a) with a plurality of (i) detectably labeled, (ii) unlabeled, monoclonal antibodies, each of which are selected from the group consisting of (i) monoclonal antibodies which specifically bind to an epitope of an activated ras protein having an amino acid substitution of arginine, glutamic acid, aspartic acid, serine, valine or cysteine at position 12 but do not bind to an epitope containing glycine at position 12, (ii) monoclonal antibodies which specifically bind to an epitope of an activated ras protein having an amino acid substitution of arginine, aspartic acid or valine at position 13, but do not bind to an epitope containing glycine at position 13, and (iii) monoclonal antibodies which specifically bind to an epitope of an activated ras protein having an amino acid substitution of histidine, lysine, leucine or arginine at position 61, but do not bind to an epitope containing glutamine at position 61, the monoclonal antibody capable of binding to an epitope on the activated ras p21 which is both different from any epitope with which the capture reagent reacts and is not present in normal ras p21; and (c) detecting either (i) the unlabeled monoclonal antibodies with a plurality of labeled antibodies specific for the unlabeled monoclonal antibodies, or (ii) the labeled monoclonal antibodies, within one of the reaction products of step (b) so as to thereby detect the activated ras p21 in the bodily fluid.

5. The immunoassay of claim 4, wherein the monoclonal antibodies are selected from the group consisting of (i) monoclonal antibody produced by a hybridoma selected from the group consisting of hybridoma DWP (ATCC Accession No. HB 8698), hybridoma E184 (ATCC Accession No. HB 9194), hybridoma E170 (ATCC Accession No. HB 9195), hybridoma R256 (ATCC Accession No. HB 9196), hybridoma D113 (ATCC Accession No. HB 10086), hybridoma D205 (ATCC Accession No. HB 10061), hybridoma D210 (ATCC Accession No. HB 10083), hybridoma S1107-8.3 (ATCC Accession No. HB 10060), hybridoma C-1119-9 (ATCC Accession No. HB 10084) and hybridoma C-1119-10 (ATCC Accession No. HB 10088); (ii) monoclonal antibody produced by a hybridoma selected from the group consisting of hybridoma D753-13(129) (ATCC Accession No. HB 9632), hybridoma D765-13(146) (ATCC Accession No. HB 9633), and hybridoma V647-13 (ATCC Accession No. HB 9634); and (iii) monoclonal antibody produced by a hybridoma selected from the group consisting of hybridoma R61-1 (ATCC Accession No. HB 10063), hybridoma R61-2 (ATCC Accession No. HB 10069), hybridoma R61-3 (ATCC Accession No. HB 10071), hybridoma R61-4 (ATCC Accession No. 10062), hybridoma L61-1 (ATCC Accession No. HB 10068), hybridoma L61-2 (ATCC Accession No. HB 10073), hybridoma H61-1 (ATCC Accession No. HB 10070), hybridoma H61-2 (ATCC Accession No. HB 10092), hybridoma H61-3 (ATCC Accession No. 10089), hybridoma H61-4 (ATCC Accession No. 10087), and hybridoma H61-5 (ATCC Accession No. HB 10090).

6. The immunoassay of claim 4 or 5, wherein the body fluid is plasma.

* * * * *